United States Patent
Abe et al.

[11] Patent Number: 6,083,368
[45] Date of Patent: *Jul. 4, 2000

[54] PROBE DEVICE FOR CONTINUOUS MEASUREMENTS OF OXYGEN IN RUNNING MOLTEN METAL

[75] Inventors: Kazuya Abe, Chiba; Seiji Sasaki, Shizuoka; Hajime Yamashita, Shizuoka-ken; Hisao Ikawa; Yukio Kanagawa, both of Osaka, all of Japan

[73] Assignee: Kawaso Electric Industrial Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/840,454

[22] Filed: Apr. 18, 1997

[30] Foreign Application Priority Data

Apr. 20, 1996 [JP] Japan ................................. 8-122169
Apr. 20, 1996 [JP] Japan ................................. 8-122170

[51] Int. Cl.[7] ................................................ G01N 27/411
[52] U.S. Cl. .......................................... 204/422; 205/784
[58] Field of Search ................................... 204/421–429; 205/783.5, 784, 784.5, 785

[56] References Cited

U.S. PATENT DOCUMENTS

| | | | |
|---|---|---|---|
| 3,705,089 | 12/1972 | Grubb | 204/435 |
| 3,723,279 | 3/1973 | Fruehan et al. | 204/428 |
| 3,773,641 | 11/1973 | Fitterer | 204/423 |
| 3,791,954 | 2/1974 | Noda et al. | 204/423 |
| 3,864,232 | 2/1975 | Handman et al. | 204/422 |
| 4,159,234 | 6/1979 | Eifler et al. | 204/428 |
| 4,186,072 | 1/1980 | Blumenthal et al. | 204/428 |
| 4,297,192 | 10/1981 | Shinohara et al. | 204/428 |
| 4,591,422 | 5/1986 | Kato et al. | 204/428 |
| 4,944,861 | 7/1990 | Reber | 204/428 |
| 5,284,570 | 2/1994 | Savage et al. | 204/422 |

*Primary Examiner*—T. Tung
*Attorney, Agent, or Firm*—Oblon, Spivak, McClelland, Maier & Neustadt, P.C.

[57] ABSTRACT

An external conductive protection tube has in a front half wall thereof a front opening formed therein with a front open area large enough to leave molten metal running in due course to inflow therethrough inside the protection tube and advance as it moves, substantially passing by a dipped length of a solid electrolyte tube installed in the protection tube, spreading between the tubes, and in a rear half wall thereof a rear opening formed therein with a rear open area large enough to leave the inflowing molten metal advancing as it moves to pass therethrough, flowing outside the protection tube.

6 Claims, 19 Drawing Sheets

FIG.8A
FIG.8B
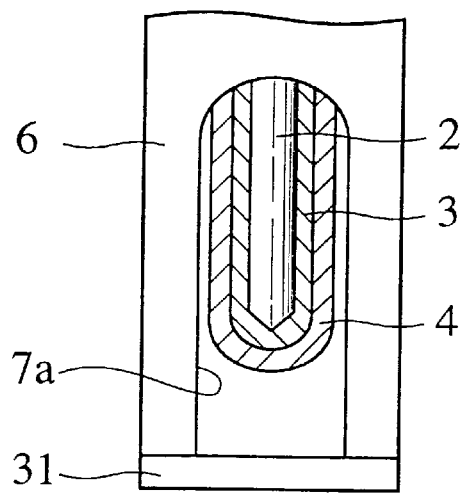
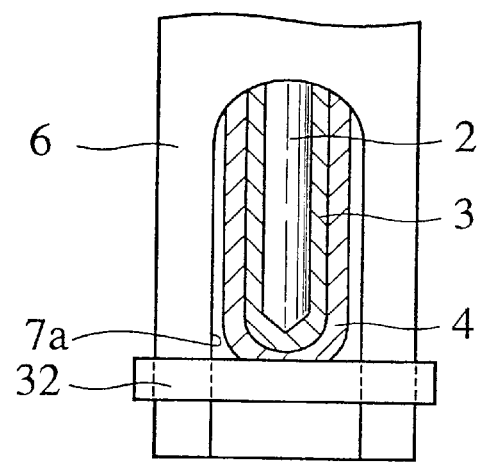

PROBE DEVICE FOR CONTINUOUS MEASUREMENTS OF OXYGEN IN RUNNING MOLTEN METAL

BACKGROUND OF THE INVENTION

1. Field of the Invention

The present invention generally relates to a probe device and a method for a continuous measurement of oxygen in molten metal, and particularly, it relates to a prove device and a method for continuously measuring over a relatively long time interval a quantity of oxygen in a running body of molten metal such as of copper.

2. Description of Relevant Art

In production, such as of a copper wire, employing a continuous casting and rolling method, there usually is observed a tendency for a body of molten metal for a continuous casting to have a violently varying oxygen concentration. There is thus needed, in the casting, a measurement of oxygen concentration to be continuously performed to ensure a secured quality in articles. For such a reason, there have been proposed various probes for measuring an oxygen concentration in molten metal.

For example, Japanese Utility Model Publication No. 63-11646 has disclosed an oxygen continuous-measuring probe in which a solid electrolyte tube has at a close end thereof a temperature moderating layer of an identical electrolyte material, a reference electrode for use in detection of an electromotive force (hereafter "emf") representative of an oxygen concentration in a body of hot atmosphere or molten metal, and a thermocouple installed in the reference electrode for detecting a varying temperature of the body.

Japanese Utility Model Publication No. 2-40536 has disclosed a probe for measuring an oxygen concentration in molten metal, in which a solid electrolyte tube has an exposed close end part thereof protected by a filter formed with a multiplicity of sufficiently small perforations for completely preventing a slag invasion, permitting part of molten metal to soak therethrough. The filter may be cooperative with an external protection tube to constitute a totally enclosing protector. However, in a concerned field of art, this probe has a limited application to a relatively short measurement, because of a possible blocking due to binding slag in a continued use.

Further, FIG. 1 shows another conventional probe for measuring a quantity of oxygen in molten metal. As shown in FIG. 1, the conventional probe has in a radially central portion thereof a solid electrolyte tube 73 close at a lower end. The close end of the electrolyte tube 73 is connected at the inside to a lead 74 such as of a platinum wire. Provided around a wall of the tube 73 is an external protection tube 71 that protects tube 73 and serves as an external electrode. A lower part of the solid electrolyte tube 73 is fixed inside the external protection tube 71, with a binding body 72 of fixative material such as a refractory cement filled therebetween. A voltmeter 79 is connected between an upper end of the protection tube 71 and one end of the lead 74 of which the other end is connected to the lower end of the electrolyte tube 73.

The probe of FIG. 1 has a body of fixative material filling inside the lower part of protection tube 71, as described. Such an oxygen measuring probe will be called "type A".

In the A-type oxygen measuring probe of FIG. 1, the solid electrolyte tube 73 is supplied with a body of reference gas, such as of air or oxygen gas or as a gaseous mixture containing oxygen, having a known concentration of oxygen. As a measuring lower end part of the probe is dipped in a body 75 of molten metal, there is constituted an oxygen concentration cell with the reference gas working as a reference electrode having a known oxygen partial pressure, generating an emf between inner and outer surfaces of the solid electrolyte tube 73, which emf is measured by the voltmeter 79 connected between the lead 74 and the external protection tube 71, permitting an oxygen concentration of the molten metal 75 to be calculated.

FIG. 2 shows another conventional A-type oxygen measuring probe that has been disclosed in Japanese Utility Model Application Laid-Open Publication No. 57-42947. In the conventional probe of FIG. 2, a solid electrolyte tube 84 has a body 83 of sintered material filling inside a wall thereof, and a lower end part of an insulating tube 87 fitted therein. The insulating tube 87 has a rod-shaped internal electrode 86 inserted therethrough to be in contact at its lower end with an upside of the sintered material 83. As such the measuring part of the probe is dipped in a body 85 of molten metal, there is generated an emf to be measured by a voltmeter 89 connected between an upper end of the internal electrode 86 and a protection tube 81 as an external electrode.

However, in measurement by the foregoing A-type oxygen measuring probes, a body 72, 82 of fixative material employed for fixation of solid electrolyte tube 73, 84 is dipped in the molten metal 75, 85. Therefore, the fixative material 72, 82 reacts on the molten metal 75, 85, dissolving therein as impurities, thus resulting in a degraded quality of articles produced therefrom. Moreover, in a case the fixative material consists of an insufficiently heat-resistive cement, there develop cracks during continuous measurement, causing molten metal to invade thereinto, giving rise to a system of irregular circuits. As a result, the conventional A-type probes tend to suffer from a progressively increasing difficulty of measuring an exact emf, thus having a limited application to very short measurements. Further, the solid electrolyte tube 73, 84 has its lower end projecting under a lower edge of the protection tube 71, 81, which lower end may be easily damaged.

As a countermeasure to such issues, a production line of an A-type oxygen measuring probe is subjected to a sampling inspection at or after a starting of each repeated run of the line, where a sampled article is dipped in molten metal for a limited short time to measure an oxygen concentration therein at intervals of a predetermined period, so that the oxygen concentration is measured a number of times for the inspection, before a necessary disposal of the sampled article. Such a production costs dear. Moreover, in a long-lasting run of the production line, the molten metal employed for the inspection may have a varying oxygen concentration with a difficulty even for an artisan to instantly cope with. Further, such a line is inadaptive for a continuous long production of articles with oxygen contained to some extent for a secured performance.

In addition, to overcome such issues, there has been proposed an oxygen measuring probe (hereafter called "type B") having residual gas in a space defined under a body of fixative material, as shown in FIG. 3. In this figure, a solid electrolyte tube 73 is fixed inside an external protection tube 71, with a binding body 72 of fixative material filled therebetween above a level upwardly off from a lower edge of the protection tube 71, thereby defining a space 76 around a lower end part of the electrolyte tube 73, to have a body of residual gas left therein when the probe is dipped in a body 75 of molten metal. In measurement, an emf is read on a voltmeter 79 connected between an upper end of the protection tube 71 and one end of a lead 74 of which the other end is connected to an inner bottom of the lower end part of the electrolyte tube 73.

Such the B-type oxygen measuring probe is allowed to overcome the discussed issues. However, when a measuring part of the probe is dipped in the molten metal 75, the electrolyte tube 73 yet suffers an unstable contact with the molten metal 75. In particular, when the molten metal 75 flows or runs, the tube 73 has little chance to contact with fresh part or layer of the molten metal 75 that has not been brought into contact, thus failing to exactly measure a continuously varying concentration of oxygen in the molten metal 75.

To overcome such shortcomings of the A-type and B-type probes, there has been proposed another conventional oxygen measuring probe (hereafter called "type C") in Japanese Patent Application Laid-Open Publication No. 55-98351, in which an external protection tube 71 has a slit or thru-hole formed in a lower end part thereof as shown in FIGS. 4 and 5A to 5C. In the C-type oxygen measuring probe shown, a solid electrolyte tube 73 is fixed in position so that its lower end does not project under a level of a lower edge of an external protection tube 71. Moreover, the protection tube 71 has a small space 76 defined inside a lower end part thereof for a body of residual gas to be left there. Further, as best shown in FIGS. 5A to 5C, the lower end part of the tube 71 is formed with a narrow and short slit 77 or a pointed thru-hole 78, as necessary for a stable contact of molten metal 75 with the lower end of the electrolyte tube 73. In measurement, an emf is read on a voltmeter 79 connected between an upper end of the protection tube 71 and one end of a lead 74 of which the other end is connected to an inner bottom of the lower end part of the electrolyte tube 73.

In the conventional C-type probe, the electrolyte tube 73 is allowed to have an improved contact with the molten metal 75 due to an enhanced displacement thereof.

However, in practical application to a runner through which hot, viscous and weighty molten metal runs at a speed toward a continuous casting and rolling section, the C-type probe still has part of molten metal stagnant in the protection tube 71, with occasionally generated and gradually growing cores of slag floating alongside walls of both tubes 71, 73, adversely affecting the emf to be measured, and aggregating in a vicinity of an exit slit 77 or an exit hole 78, partially stopping the slit or hole, with an increased stagnating tendency giving rise to an excessive aggregation, resulting in a failure of effective measurement before an end of a continuous long service.

No slag nor potential slag core nor foreign matter should enter in a protection tube, which has been a common recognition to the artisan. Accordingly, the smaller a front slit or a front hole is set, the better it appears.

Moreover, the lower end part of the protection tube 71 is relatively short so that the body of residual gas left in the space 76 has a limited volume and a limited vertical thickness under normal condition. The thickness becomes still smaller, as the lower end part of the probe is submerged to an increased depth. At a desirable depth, a flattened body of residual gas may be easily broken by an occasional weighty irregular action such as a surfacial protrusion of running molten metal, so that the molten metal may lick the fixative material 72 from time to time.

Further, in each of the foregoing conventional probes, the external protection tube needs a sufficient rigidity to stand, all the way of a continuous long service, with an integration of dynamic pressures substantially over an entire front wall receiving ceaselessly surging streams of weighty molten metal, in addition to that the molten metal is hot enough to make a dipped part of the protection tube gradually flexible or flexed. A necessary wall thickness renders a cost dear, as an employable material is of value.

Still more, in each conventional case described, it is impossible to reuse a dipped member, as so believed in the field of endeavor.

SUMMARY OF THE INVENTION

The present invention has been achieved with such points in mind.

It therefore is a first object of the present invention to provide a probe device and a method for a continuous measurement of oxygen in a running body of molten metal, in which an external protection member allows natural or deflected streams of the molten metal to pass therethrough, taking an invasion of slag or foreign matter easy, without unfavorable stagnant part, permitting an effectively reduced wall area to stand with dynamic pressures of the molten metal as well as an effectively reduced quantity of valued material to be employed.

It is a second object of the invention to provide a probe device and a method for a continuous measurement of oxygen in a running body of molten metal, in which a body of fixative material is allowed to be free from unfavorable contact with the molten metal even when the probe is dipped to a favorable depth that may be a bottom of a runner.

It is a third object of the invention to provide a probe device and a method for a continuous measurement of oxygen in a running body of molten metal, in which an external protection member is allowed to have an effectively increased rigidity, permitting a continuous long service.

It is a fourth object of the invention to provide a probe device and a method for a continuous measurement of oxygen in a running body of molten metal, in which an external protection member is allowed to be partially reused, permitting a reduced cost.

It is a fifth object of the invention to provide a probe device for a continuous measurement of oxygen in a running body of molten metal, in which an external protection member has a defined ideal configuration with absolute dimensions permitting a continuous long, precise and stable measurement.

It is a sixth object of the invention to provide a probe device for a continuous measurement of oxygen in a running body of molten metal, in which an external protection member has a defined ideal configuration with dimensional proportions permitting a continuous long, precise and stable measurement.

To achieve the first object, according to a first aspect of the invention, there is provided a probe device for a continuous measurement of oxygen in a running body of molten metal, the probe device comprising: a first tube member made of a solid electrolyte material and close at a lower end thereof; a reference electrode contacted on an inside of the first tube member; detection means for detecting a potential difference between a first node connected to the reference electrode and a second node; a conductive second tube member connected to the second node, the second tube member enclosing the first tube member for an external protection, the second tube member having a first wall at a side thereof facing streams of the running body of molten metal when dipped therein and a second wall at another side thereof; a first opening formed in the first wall with a first open area large enough to leave part of the running body of molten metal running in due course to inflow therethrough inside the second tube member and advance as it runs, substantially passing by a dipped length of the first tube member, spreading between the first and second tube members; and a second opening formed in the second wall with a second open area as large as the first open area so that the inflowing part of molten metal is left as it advances to pass therethrough, flowing outside the second tube member.

According to the first aspect, as a first tube member enclosed by a second tube member for an effective external protection is dipped in running molten metal into a depth for a normal measurement length of the first tube member to be submerged, there is generated an oxygen concentration cell across a wall of the first tube member between a reference electrode and part of the molten metal inflowing inside the second tube member, with a corresponding emf developed therebetween as a potential difference detectable between a first node connected to the reference electrode and a second node connected to the second tube member that is conductive.

The inflowing part of molten metal is left as it runs at an associated speed, so it enters inside the second tube member through a first opening formed in a wall region at a side of the second tube member called "first wall", and advances, substantially passing by a dipped length of the first tube member, spreading between the first and second tube members, and in due course it passes through a second opening formed in a wall region at another side of the second tube member called "second wall", flowing outside the second tube member.

Some pieces of slag or foreign matter may triumphantly come in to simply go out.

The first opening has a sufficiently large open area, and the second opening also. Such areas are mere vacant bodies. But, they ideally absorb dynamic and static pressures acting thereon. Moreover, they cost little.

According to a second aspect of the invention, as it depends from the first aspect, the streams of the running body of molten metal comprise natural streams thereof.

According to the second aspect, a first wall may preferably comprise a front wall that opposes natural streams of running body of molten metal.

According to a third aspect of the invention, as it depends from the first aspect, the streams of the running body of molten metal comprise deflected streams thereof.

According to the third aspect, a first wall may preferably comprise a bottom or side wall that faces deflected streams of running molten metal. A deflector may comprise a bulge or recess formed in the first wall, or a corner, a curve or a surface provided in a runner.

According to a fourth aspect of the invention, as it depends from the first aspect, one of the first and second openings is shaped in one of a circular form, a rectangular form and a bell form.

In this respect, the openings may be otherwise configured in consideration of a nature, an average and/or local speed, an average and/or local temperature, and/or a running or deflected direction of molten metal, a depth and/or a width of a molten metal runner, an average size of probable slag or foreign matter, and/or a rigidity and/or a strength of a first and/or a second tube member.

According to a fifth aspect of the invention, as it depends from the first aspect, one of the first and second openings is open at a lower end thereof.

According to a sixth aspect of the invention, as it depends from the first aspect, the first wall has a plurality of those first openings formed therein.

According to a seventh aspect of the invention, as it depends from the sixth aspect, the plurality of first openings are vertically aligned.

According to an eighth aspect of the invention, as it depends from the sixth aspect, the plurality of first openings are horizontally aligned.

According to a ninth aspect of the invention, as it depends from the first or the sixth aspect, the second wall has a plurality of those second openings formed therein.

Moreover, to achieve the second object described, according to a tenth aspect of the invention, as it depends from the first aspect, the probe device further comprises: an insulating rigid member fixed directly or indirectly to the second tube member; and a body of fixative material for fixing an upper end of the first tube member to the rigid member.

According to the tenth aspect, a fixative material is permitted to be placed upwardly off at a distance from a surface of molten metal, to avoid a licking by the molten metal.

According to an eleventh aspect of the invention, as it depends from the tenth aspect: the rigid member has a conductive sheath member inserted therethrough and connected at a lower end thereof to the reference electrode and at an upper end thereof to the first node; and the sheath member has a thermocouple inserted therethrough, with a body of insulating material filled therebetween.

According to a twelfth aspect of the invention, as it depends from the eleventh aspect: the thermocouple comprises a pair of wires connected at lower ends thereof both to the reference electrode and at upper ends thereof either to both a third node and a fourth node; and the detection means detects a potential difference between the third and fourth nodes.

According to a thirteenth aspect of the invention, as it depends from the twelfth aspect, the potential difference between the first and second nodes represents an emf of an oxygen concentration cell between the reference electrode and the inflowing part of molten metal.

According to a fourteenth aspect of the invention, as it depends from the thirteenth aspect, the potential difference between the third and fourth nodes represents a temperature of the inflowing part of molten metal.

Further, to achieve the third object described, according to a fifteenth aspect of the invention, as it depends from the first aspect, the probe device further comprises a rigid member for reinforcing the second tube member.

According to a sixteenth aspect of the invention, as it depends from the fifteenth aspect, the rigid member comprises a plate member provided at a lower end of the second tube member.

According to a seventeenth aspect of the invention, as it depends from the sixteenth aspect: the second tube ember is circular in section; and the plate member comprises a disc plate fixed to a circular edge at the lower end of the second tube member.

According to an eighteenth aspect of the invention, as it depends from the seventeenth aspect, the disc plate has an identical outside diameter to the circular edge.

According to a nineteenth aspect of the invention, as it depends from the seventeenth aspect, the disc plate is fitted in the circular edge.

According to a 20th aspect of the invention, as it depends from the seventeenth aspect, the disc plate is formed with a central opening.

According to a 21st aspect of the invention, as it depends from the sixteenth aspect, the plate member has an edge part partially defining one of the first and second openings.

According to a 22nd aspect of the invention, as it depends from the fifteenth aspect, the rigid member comprises an elongate member fixed to a lower end of the second tube member.

According to a 23rd aspect of the invention, as it depends from the 22nd aspect, the elongate member extends substantially in parallel to one of the first and second openings.

According to a 24th aspect of the invention, as it depends from the 22nd aspect, the elongate member extends substantially in perpendicular to one of the first and second openings.

According to a 25th aspect of the invention, as it depends from the fifteenth aspect, the rigid member is shaped in a Y-form.

According to a 26th aspect of the invention, as it depends from the fifteenth aspect, the rigid member is shaped in a cross form.

According to a 27th aspect of the invention, as it depends from the fifteenth aspect, the rigid member is shaped in a zigzag form.

Furthermore, to achieve the fourth object described, according to a 28th aspect of the invention, as it depends from the first aspect, the probe device further comprises: a rigid member slidable and fixative relative to the first tube member; and the second tube member being screwed at a vertically mediate part thereof to the rigid member.

According to the 28th aspect, the second tube member may be separable at the mediate part to replace a lower dipped part with a new one.

Furthermore, to achieve the fourth object described, according to a 29th aspect of the invention, as it depends from the first aspect, the second tube member is long enough to be cut for a reuse.

According to the 29th aspect, a stained or deformed part may be cut to be disposed, as the rest serves for a subsequent measurement.

Still more, to achieve the fifth object described, according to a 30th aspect of the invention, as it depends from the first aspect: the probe device further comprises a sheathed thermocouple inserted as an inner electrode in the first tube member, and a reinforcement member attached to a lower end part of the second tube member; the reference electrode comprises a body of reference material filled in the first tube member, the reference material consisting of a metal and an oxide thereof; the second tube member serves as an external electrode; and the first and second openings each comprise one of a slot and a thru-hole.

According to the 30th aspect, for a continuous measurement of oxygen, there is provided a probe device having in a measuring portion thereof a protection tube of which a distal end part is formed with a plurality of slots or thru-holes of an adequate configuration (e.g. circle, ellipse, etc) and provided with a reinforcement member, thus allowing the device to serve for the continuous measurement over a relatively long interval of time, with a secured prevention such as against an unfavorable reduction in slot size due to a deformation of the protection tube or against damages to or a rupture of that tube or a solid electrolyte tube, as well as allowing part of molten metal residing inside the protection tube to be naturally replaced with part thereof coming downstream, permitting the electrolyte tube to be always contacted with this fresh part of molten metal, resulting in an oxygen measurement at a high accuracy.

For an ensured prevention of molten metal stagnation and for an enhanced replacement of molten metal, a pair of slots or thru-holes may preferably be located in a mirror-imaged manner or in symmetry with respect to a vertical plane passing a center of the protection tube. However, streams of molten metal may be rough so that a severe symmetry may sometimes be redundant.

According to a 31st aspect of the invention, as it depends from the 30th aspect: the slot has an arcuate width not smaller than 2 mm along an outer circumference of the second tube member; a total number of those slots have a sum of respective those arcuate widths thereof not exceeding a 70% of a length of the outer circumference; the thru-hole has an arcuate diameter not smaller than 2 mm along the outer circumference; and a total number of those thru-holes have a sum of respective those arcuate diameters thereof not exceeding the 70% of the length of the outer circumference.

According to the 31st aspect, there is disclosed a preferable range of opening size based on empirical data.

According to a 32nd aspect of the invention, as it depends from the 30th or the 31st aspect, the probe device further comprises: an internal protection tube provided inside the second tube member, the internal protection tube serving as an insulator at an upper end of the first tube member, for holding the first tube member free of contact with the second tube member.

According to the 32nd aspect, an insulating internal protection tube is provided at an upper end of a solid electrolyte tube, permitting an indirect fixing of this tube relative to an external protection tube, as well as an increased effect for the prevention against damages or rupture.

According to a 33rd aspect of the invention, as it depends from the 30th or the 31st aspect, the lower end of the first tube member has a lower position than an upper end of that one of the slot and the thru-hole.

According to the 33rd aspect, a solid electrolyte tube has an exposed part with an increased tendency to be contacted with fresh part of running molten metal.

Yet more, to achieve the sixth object described, according to a 34th aspect of the invention, as it depends from the first aspect: the probe device further comprises a sheathed thermocouple inserted as an inner electrode in the first tube member; the reference electrode comprises a body of reference material filled in the first tube member, the reference material consisting of a metal and an oxide thereof; the second tube member serves as an external electrode; and the first and second openings each comprise one of a slot and a thru-hole, the slot having a width thereof within a range between a ¼ of an outside diameter of the first tube member and a ⅓ of an outside diameter of the second tube member, the thru-hole having a diameter thereof within the range.

According to the 34th aspect, for a continuous measurement of oxygen, there is provided a probe device having in a measuring portion thereof a protection tube that is formed at a distal end part thereof with a plurality of slots or thru-holes of a configuration with an adequate size, so that part of molten metal inside the protection tube is naturally replaced with part thereof coming from outside, permitting an electrolyte tube to be always contacted with fresh part of molten metal, resulting in an oxygen measurement at a high accuracy.

Yet more, to achieve the sixth object described, according to a 35th aspect of the invention, as it depends from the first aspect: the probe device further comprises a sheathed thermocouple inserted as an inner electrode in the first tube member, and a reinforcement member attached to a lower end part of the second tube member; the reference electrode comprises a body of reference material filled in the first tube member; the second tube member serves as an external electrode; and the first and second openings each comprise one of a slot and a thru-hole, the slot having a width thereof within a range between a 1/5 of an outside diameter of the first tube member and a 3/5 of an outside diameter of the second tube member, the thru-hole having a diameter thereof within the range.

According to the 35th aspect, an external protection tube is provided with a reinforcement member attached to a lower end part thereof, which is thus permitted to have an enlarged slot or thru-hole formed therein.

According to a 36th aspect of the invention, as it depends from the 34th or the 35th aspect: the first tube member has an exposed length in the slot; and the slot has a ratio of a length thereof to the exposed length within a range between 7:1 and 7:6.

According to the 36th aspect, there is disclosed a preferable size range of a slot in terms of a ratio of a height of the slot to an exposed length of a solid electrolyte tube.

According to a 37th aspect of the invention, as it depends from the 34th or the 35th aspect, the probe device further comprises an internal protection tube provided inside the second tube member for covering part of the sheathed thermocouple lead out of the first tube member, the internal protection tube being fitted to be fixed at a lower end thereof to an upper end of the first tube member.

According to the 37th aspect, a solid electrolyte tube is indirectly fixed to an external protection tube.

According to a 38th aspect of the invention, as it depends from the 35th aspect, the reinforcement member comprises one of a rod-like member and a plate-like member that bridges points of the lower end part of the second tube member between respective those slots.

According to the 38th aspect, an external protection tube may be effectively reinforced in a manner easy of stress calculation.

According to a 39th aspect of the invention, as it depends from the 35th aspect, the probe device further comprises: processing means for processing data on the potential difference representative of an electromotive force and a temperature signal to determine an oxygen activity and a temperature of the molten metal; and one of first display means for displaying temporal values of the oxygen activity and the temperature of the molten metal and second display means for displaying the oxygen activity.

According to the 39th aspect, a processor for an arithmetic operation serves for processing a molten metal temperature signal and an emf data, as they are obtained by dipping a measuring portion of a probe device, to calculate a molten metal temperature and an oxygen activity in consideration thereof. Calculated values are displayed, as necessary. The measuring portion may be provided at one or more places along a molten metal runner, and one or more displays may be placed along a production line including a casting and rolling section, permitting necessary data to be informed in a real-time manner, for production of articles with a secured quality at a high accuracy.

Still further, to achieve the first object, according to a 40th aspect of the invention, there is provided a probe device for a continuous measurement of oxygen in a running body of molten metal, the probe device comprising: a first tube member made of a solid electrolyte material and close at a lower end thereof; a reference electrode contacted on an inside of the first tube member; detection means for detecting a potential difference between a first node connected to the reference electrode and a second node; a conductive second tube member connected to the second node, the second tube member enclosing the first tube member for an external protection, the second tube member having a first wall at a side thereof facing streams of the running body of molten metal when dipped therein and a second wall at another side thereof; first opening means formed in the first wall with a first open area large enough to leave part of the running body of molten metal running in due course to inflow therethrough inside the second tube member and advance as it runs, substantially passing by a dipped length of the first tube member, spreading between the first and second tube members; and second opening means formed in the second wall with a second open area not smaller than the first open area so that the inflowing part of molten metal is left as it advances to pass therethrough, flowing outside the second tube member.

According to the 40th aspect, a first opening means may comprise one or more sufficiently large first openings, and a second opening means may comprise one or more sufficiently large second openings. The term "means" means including additive or auxiliary measures for causing molten metal to positively and/or smoothly flow through an external protection tube, such as a chamfered opening edge, a tapered cut face, a bulge or recess, an additional path around or through a wall, a deflector, etc.

Yet further, to achieve the first object described, according to a 41st aspect of the invention, there is provided a method for a continuous measurement of oxygen in a running body of molten metal, the method comprising the steps of: having a first tube member made of a solid electrolyte material and close at a lower end thereof; having a reference electrode contacted on an inside of the first tube member; having a conductive second tube member connected to a first node, the second tube member enclosing the first tube member for an external protection, the second tube member having a first wall at a side thereof facing streams of the running body of molten metal when dipped therein and a second wall at another side thereof; having a first opening formed in the first wall with a first open area; having a second opening formed in the second wall with a second open area as large as the first open area; leaving part of the running body of molten metal running in due course to inflow through the first opening inside the second tube member and advance as it runs, substantially passing by a dipped length of the first tube member, spreading between the first and second tube members; leaving the inflowing part of molten metal advancing to pass through the second opening, flowing outside the second tube member; and detecting a potential difference between the first node and a second node connected to the reference electrode.

Yet further, to achieve the first object described, according to a 42nd aspect of the invention, there is provided a method for a continuous measurement of oxygen in a running body of molten metal, the method comprising the steps of: having a first tube member made of a solid electrolyte material and close at a lower end thereof; having a reference electrode contacted on an inside of the first tube member; having a conductive second tube member connected to a first node, the second tube member enclosing the first tube member for an external protection, the second tube member having a first wall at a side thereof facing streams of the running body of molten metal when dipped therein and a second wall at another side thereof; having first opening meanss formed in the first wall with a first open area; having second opening means formed in the second wall with a second open area not smaller than the first open area; leaving part of the running body of molten metal running in due course to inflow through the first opening means inside the second tube member and advance as it runs, substantially passing by a dipped length of the first tube member, spreading between the first and second tube members; leaving the inflowing part of molten metal advancing to pass through the second opening means, flowing outside the second tube member; and detecting a potential difference between the first node and a second node connected to the reference electrode.

Still furthermore, to achieve the first object, according to a 43rd aspect of the invention, there is provided a probe device for a continuous measurement of oxygen in a running body of molten metal, the probe device comprising: a first tube member made of a solid electrolyte material and close at a lower end thereof; a reference electrode contacted on an inside of the first tube member; detection means for detecting a potential difference between a first node connected to the reference electrode and a second node; a conductive second tube member connected to the second node, the second tube member enclosing the first tube member for an external protection, the second tube member having a first wall at a side thereof facing streams of the running body of molten metal when dipped therein and a second wall at another side thereof; first opening means formed in the first wall with a first open area large enough to leave part of the running body of molten metal running in due course to inflow therethrough inside the second tube member and advance as it moves, substantially passing by a dipped length of the first tube member, spreading between the first and second tube members; and second opening means formed in the second wall with a second open area large enough to leave the inflowing part of molten metal advancing as it moves to pass therethrough, flowing outside the second tube member.

According to any of the 40th to 43rd aspects, there are achieved similar effects to the first aspect.

Incidentally, the 31st and the 34th to 36th aspects are each directed to a preferable size range of an opening. To this point, the accuracy of measurement is variable to a certain degree with a size of the opening through which a fresh part of molten metal is brought into contact with a solid electrolyte tube. This is because the accuracy depends on how fresh the contacted part of molten metal is.

A slot and a thru-hole are now concerned, as related data will be given herein. For a desirable measurement accuracy, such an opening needs to be by far larger in width or diameter than that one which tends to undergo a blocking such as by a piece of binding slag. Preferably, the slot and the thru-hole should each have a width or a diameter over a ¼ of an OD (outside diameter) of the electrolyte tube in the 34th aspect.

The opening size affects on a strength of an external protection tube. For a desirable service, the opening should be limited in size such that a rest of the tube is strong enough to stand without significant deformations. Preferably, the slot and the thru-hole are each expected to have a width or a diameter under a ⅓ of an OD of the protection tube in the 34th aspect.

Such a size restriction may be moderated by use of a reinforcement member so that the slot and the thru-hole may preferably each have a width or a diameter within a range between a ⅕ of the OD of the electrolyte tube and a ⅗ of the OD of the protection tube in the 35th aspect, or an arcuate width or an arcuate diameter over a 2 mm in the 31st aspect, where such arcuate widths or arcuate diameters are limited in total to be under a 70% of the OD of the protection tube.

The formation of an opening in the protection tube makes the electrolyte tube partially exposed in a front view. Too short exposed part may fail to have a secured contact with molten metal. Too long exposed part may project beneath a lower end of the protection tube. The exposed part should thus have an adequate length between a 1:7 and a 6:7 in ratio to a length of the slot.

BRIEF DESCRIPTION OF THE ACCOMPANYING DRAWINGS

The above and further objects and novel features of the present invention will more fully appear from the following detailed description when the same is read in conjunction with the accompanying drawings, in which:

FIG. 8A is a partial front view of a measuring portion of an oxygen measuring probe according to a modification of the embodiment of FIG. 6;

FIG. 8B is a partial front view of a measuring portion of an oxygen measuring probe according to another modification of the embodiment of FIG. 6;

DETAILED DESCRIPTION OF THE PREFERRED EMBODIMENTS

Figure 1:
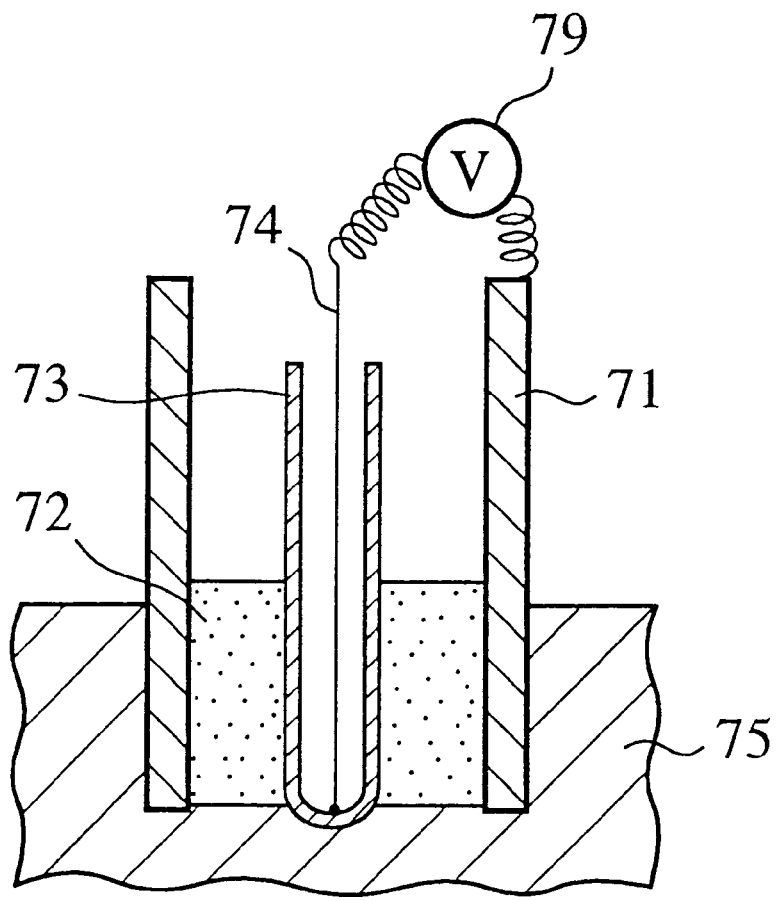
FIG. 1 is a schematic longitudinal section of a conventional oxygen measuring probe.
Figure 2:
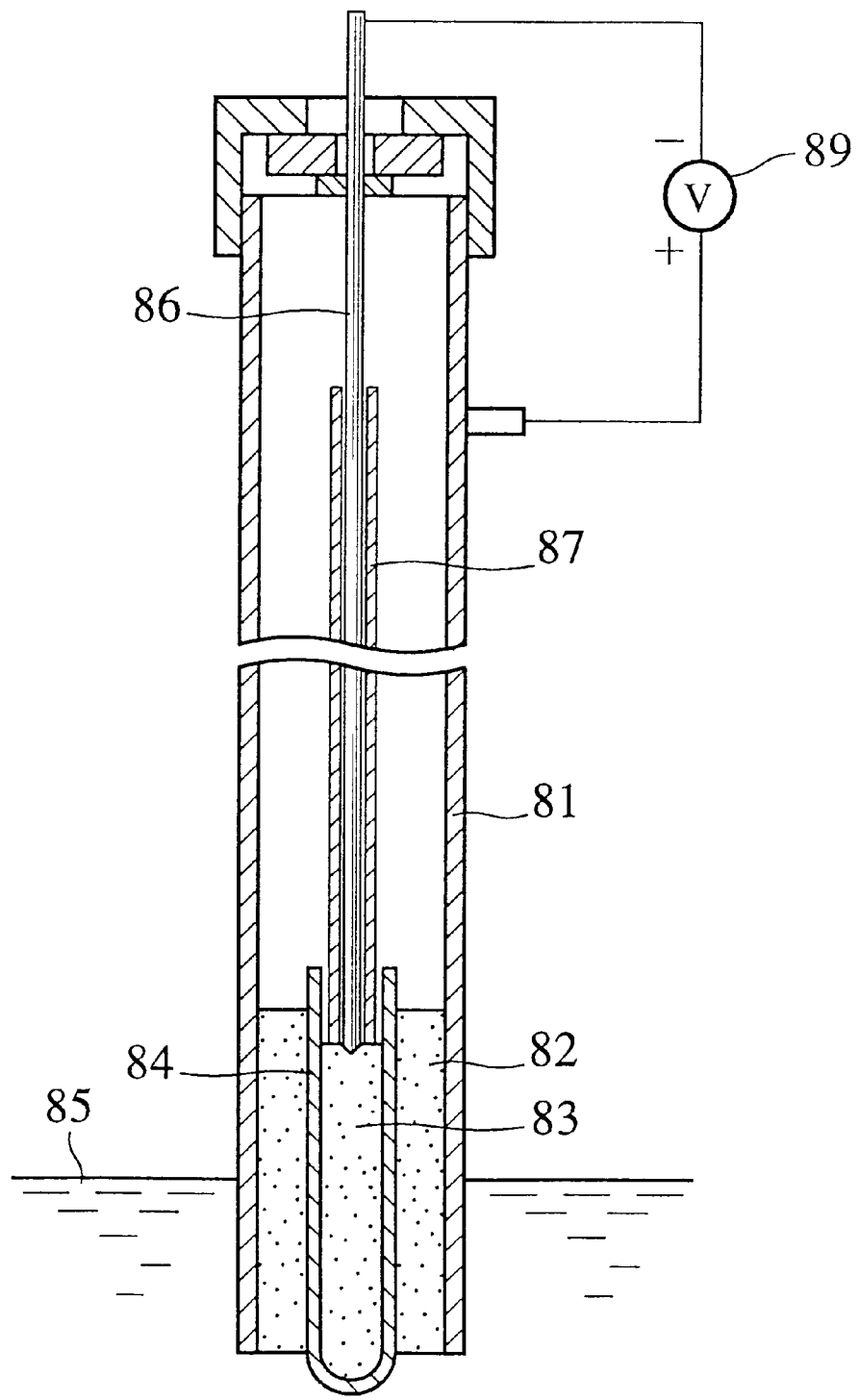
FIG. 2 is a partially cutaway longitudinal section of another conventional oxygen measuring probe.
Figure 3:
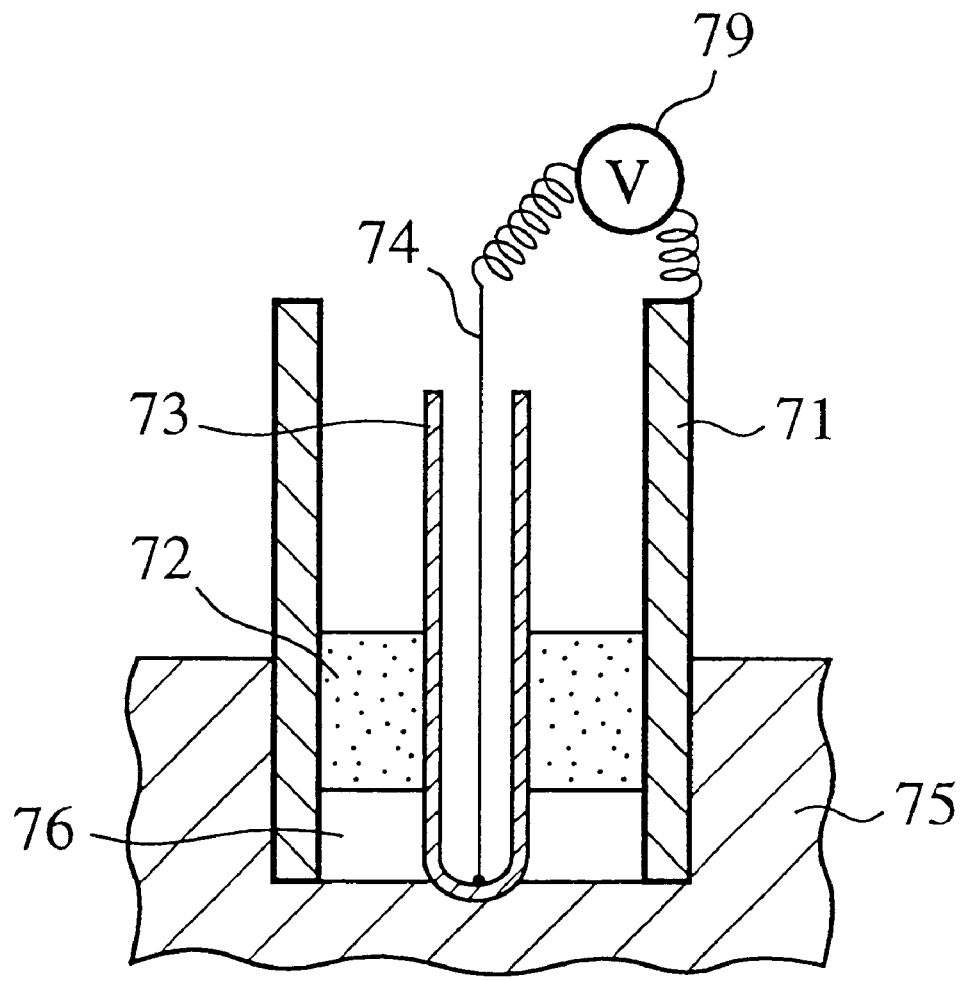
FIG. 3 is a schematic longitudinal section of another conventional oxygen measuring probe.
Figure 4:
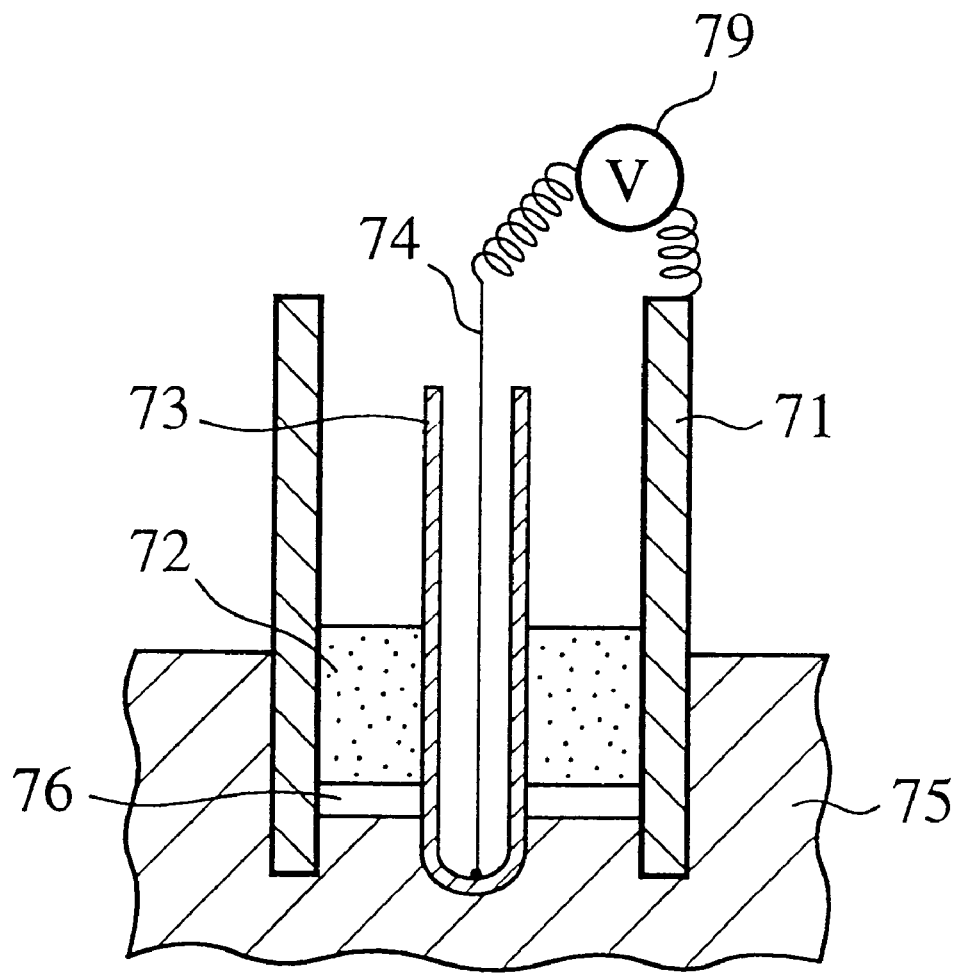
FIG. 4 is a schematic longitudinal section of another conventional oxygen measuring probe.
Figure 5A:
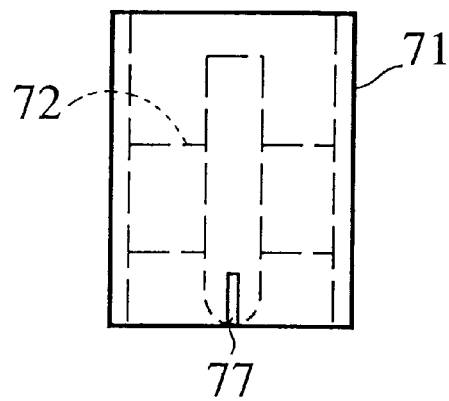
FIG. 5A is a front view of the probe of FIG. 4.
Figure 5B:
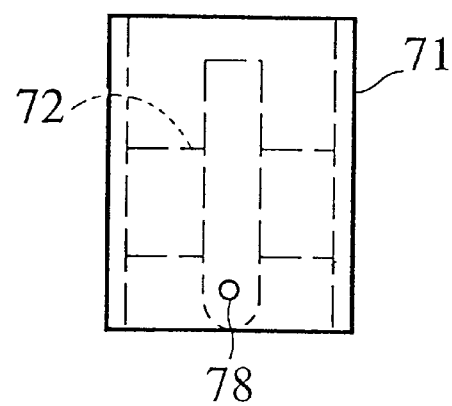
FIG. 5B is a modification of the probe of FIG. 4.
Figure 5C:
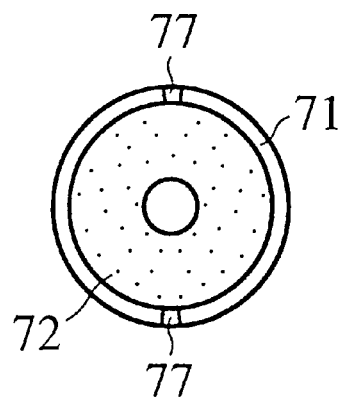
FIG. 5C is a cross section of the probe of FIG. 4.

There will be detailed below the preferred embodiments of the present invention with reference to the accompanying drawings. Like members are designated by like reference characters.

Figure 6:
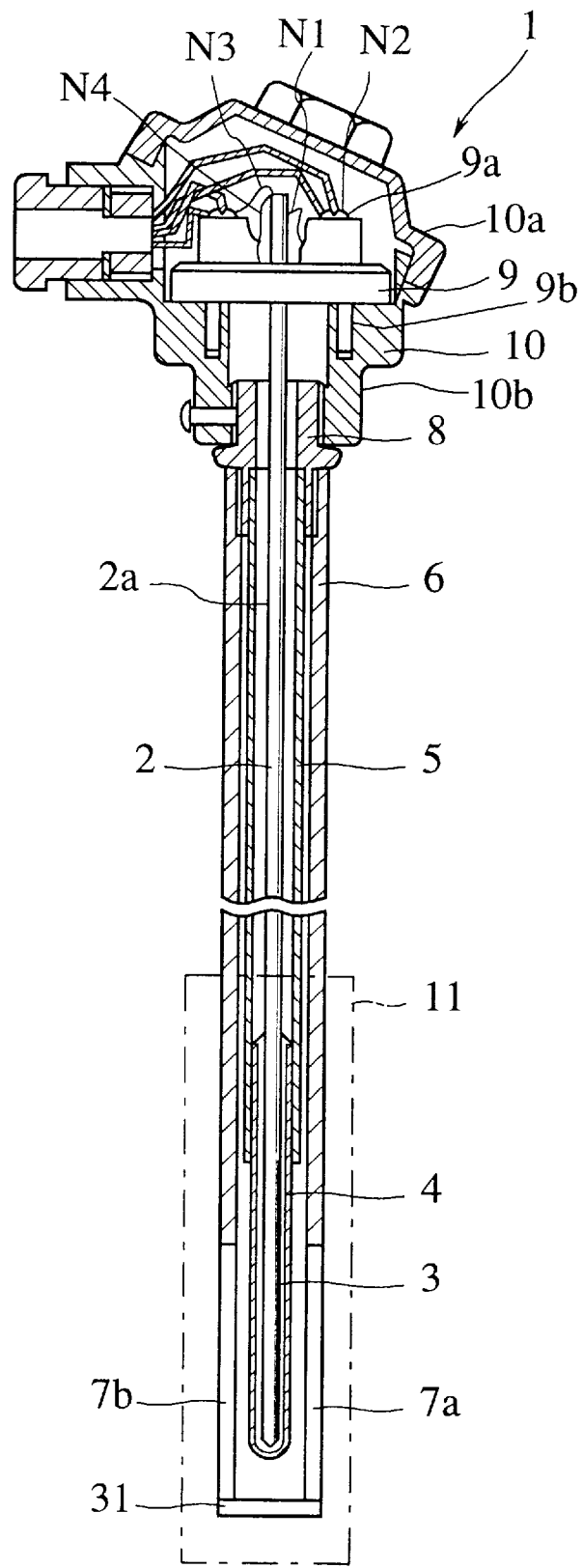
FIG. 6 is a longitudinal section of an oxygen measuring probe of a probe device according to an embodiment of the invention.
Figure 7:
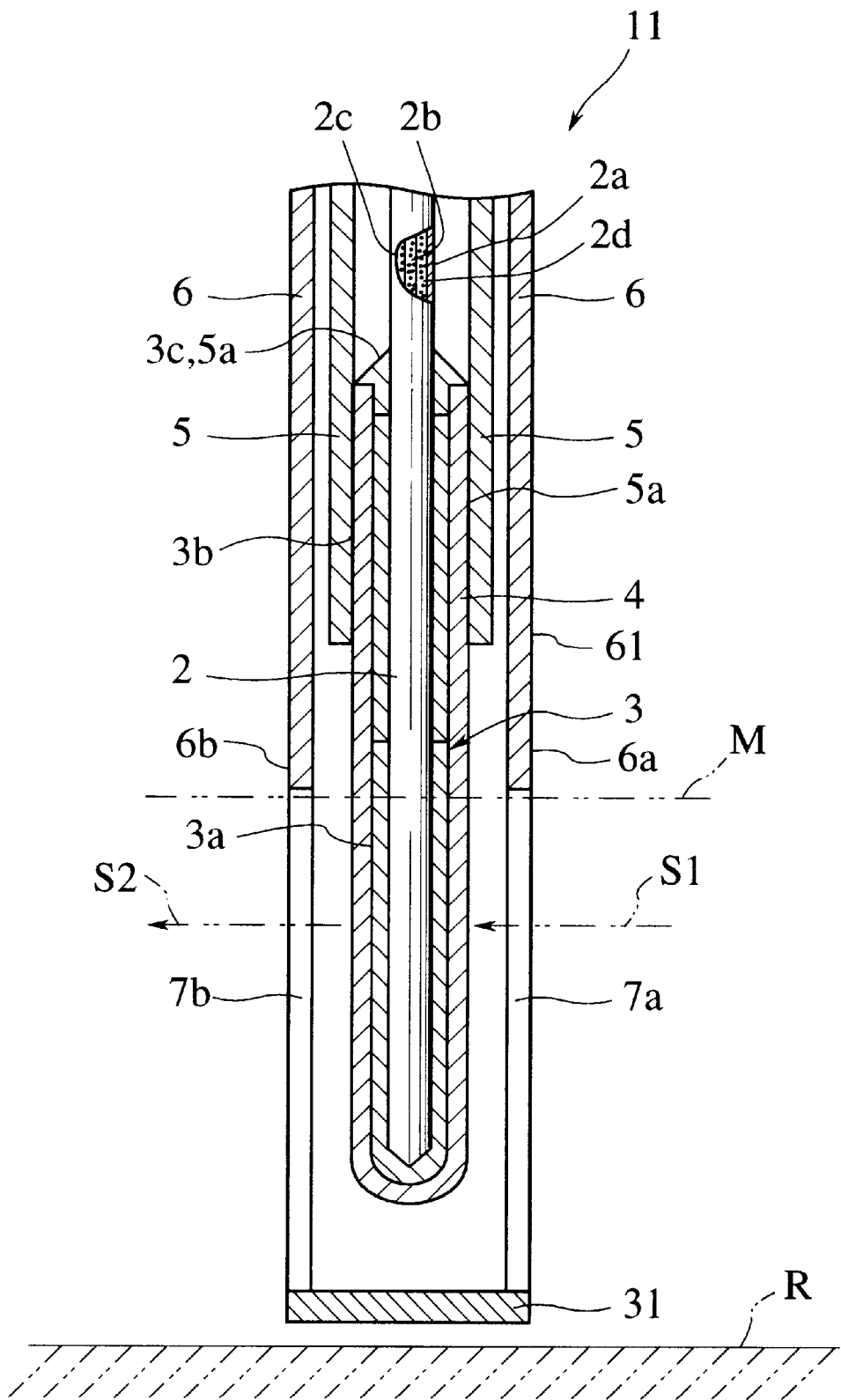
FIG. 7 is an enlarged section of a measuring portion of the probe of FIG. 6.

FIG. 6 shows an oxygen measuring probe of a probe device according to a first embodiment of the invention, and FIG. 7, a measuring portion as a sensor part of the probe.

In FIG. 6, designated at reference character 1 is the probe, and 11 is the measuring portion. The probe 1 comprises the measuring portion 11, and the rest called "terminal portion".

As shown in FIGS. 6 and 7, the measuring portion 11 includes a solid electrolyte tube 4 arranged in a central part thereof and formed to be close at its round lower end, which tube 4 has inserted therein a distal end of a sheathed thermocouple 2 that serves as an internal electrode in a later-described manner. Filled between the tube 4 and the sheathed thermocouple 2 is a body 3 of reference material consisting such as of Mo and $MoO_2$, which body 3 constitutes a reference electrode.

The sheathed thermocouple 2 upwardly extends above an upper end part of the tube 4, to have an extension lead out thereof, which extension is loose fitted in an insulating internal protection tube 5, which tube 5 has a lower end part thereof fitted on the upper end part of the electrolyte tube 4 and fixed thereon with a body 5a of fixative material such as a refractory cement.

The internal protection tube 5 as well as the electrolyte tube 4 is enclosed by a conductive external protection tube 6 of which a lower end part is formed with a pair of front and rear axial slots 7a, 7b and provided with a reinforcement member 31 attached to a bottom thereof.

In the terminal portion of the probe 1, a terminal casing 10 has a non-conductive terminal block 9 installed therein for mounting external output terminals 9a, contacts 9b and the like, including later-described nodes N1 to N4 (represented by connected elements in the figure). The casing 10 comprises an insulating upper case 10a, and a conductive lower case 10b in which a conductive hat-like socket 8 is screwed at a head part thereof. The socket 8 has a downwardly extending boss part, in which an upper end part of the insulating internal protection tube 5 is fitted to be fixed with a body of fixative material such as a refractory cement, and on which an upper end part of the conductive external protection tube 6 is screwed so that the protection tube 6 can be replaced with a new one.

The sheathed thermocouple 2 extends through a vertical opening formed in a central part of the socket 8, to have an upper end thereof fixed to or supported by the terminal block 9. The sheathed thermocouple 2 comprise: a conductive sheath 2a (FIG. 7) connected at a lower end thereof to the reference electrode 3 and at an upper end thereof to node N1 (FIG. 6); a pair of wires 2b, 2c (FIG. 7) as thermoelectrical temperature sensing metals joined at their lower ends, and connected at their upper ends to nodes N3, N4 (FIG. 6), respectively; and a body 2d (FIG. 7) of insulating material filled between the sheath 2a and the paired wires 2b, 2c. Due to a Seebeck effect, the wires 2b, 2c have a thermoelectromotive force developed therebetween to be detected as a potential difference between nodes N3, N4, which will be called a temperature signal.

On the other hand, as the measuring portion 11 of the probe 1 is partially dipped in a body of molten metal running along a runner, there is constituted an oxygen concentration cell having as a reference electrode thereof a combination of the sheath 2a of thermocouple 2 and the reference material 3 and as an external sensing electrode thereof a combination of part of the molten metal moving around a dipped length of the electrolyte tube 4 and the external protection tube 6, with an emf developed across wall of the electrolyte tube 4 which is contacted at the inside to the reference material and at the outside to the molten metal. The developed emf is detected as a potential difference between node N1 connected to the sheath 2a and node N2 connected to the protection tube 6 via contact 9b, lower case 10b and socket 8.

In the probe 1, the solid electrolyte tube 4, which is conductive, is indirectly fixed to the conductive external protection tube 6, i.e., it is fixed thereto via the insulating internal protection tube 5 and the conductive socket 8 of terminal portion. More specifically, the electrolyte tube 4 is fitted to be fixed at its upper end part in the lower end part of the insulating tube 5, with the fixative material 5a applied therebetween. The tube 4 has a relatively long body downwardly extending from the fixed upper end and enclosed by a cylindrical wall of the external protection tube 6, with an annular space left therebetween to avoid a direct contact. The fixative material 5a that may well be a refractory cement is thus kept from an occasional contact with molten metal, without an anxiety to an unfavorable mixing into molten metal. The long body of tube 4 may be dipped to a voluntary depth, permitting a sufficient contact between tube wall and molten metal to measure an oxygen concentration of molten metal with an increased accuracy. The annular space about tube 4 serves as an allowance to protect this tube 4 from an undesirable interference with the metallic external tube 6 that stands against most of dynamic pressures exerted by primary streams of running hot molten metal during a long continuous measurement and may deform, distort or flex with time. During the entirety of such a measurement, the tube 4 is thus kept from being broken or damaged by external forces such as by a deformation of external tube 6. Hence, also the sheathed thermocouple 2 is kept free from troubles such as a disconnection of element wires due to a distortion of electrolyte tube 4.

As best shown in FIG. 7, the external protection tube 6 has the slots 7a, 7b formed in front and rear wall regions 6a, 6b of a lower end part 61 thereof, as a body M of molten metal naturally runs from righthand to lefthand of the figure. The slots 7a, 7b have an individual width not smaller than 2 mm along an outer circumference of the protection tube 6 and a total width not exceeding a 70% of the outer circumference. The slot 7a on the front side may have an identical open area to or a larger or smaller open area than the slot 7b on the rear side.

In any case, the molten metal M is left as it runs along a little sloped runner R so that part of the molten metal M flows in due course to inflow through the front slot 7a inside the protection tube 6, like an arrow representing a typical stream S1, advancing as it moves or runs, substantially passing by a dipped length of the electrolyte tube 4, spreading between the tubes 4, 6.

The inflowing part of molten metal M is still left as it advances or moves to pass through the rear slot 7b, flowing outside the protection tube 6, like an arrow representing a stream S2.

Slag or foreign matter may come in together with the molten metal M, to simply go out. As the part of molten metal M directionally moving and advancing in the protection tube 6 has little tendency to be stagnant, the electrolyte tube 4 is always brought into contact over the dipped length with streams of fresh molten metal washing the wall.

To this point, the front and rear slots 7a, 7b may have their four sides tapered at a frontwardly spreading angle, and the respective sides may be chamfered over lengths of their edges. In addition, the wall may be bulged along the four or vertical two sides, and/or inwardly recessed therealong.

The front and rear slots 7a, 7b may have their dimensions changed to positively employ a difference of dynamic pressure between inside and outside the protection tube 6 for an enhanced induction or inspiration of molten metal.

To achieve an enhanced or controlled movement of molten metal, the runner R may have a corner, a deflector, and/or a varied slope. Moreover, a support structure of the probe 1 may be positively used to have activated and/or layered streams of molten metal directed toward the front slot 7a, and/or more streams drawn out of the rear slot 7b.

FIGS. 8A and 8B show measuring portions of oxygen measuring probes according to modifications of the first embodiment, respectively.

In the measuring portion of FIG. 8A, an external protection tube 6 is formed with a front slot 7a and an analogous rear slot both arcuate along their upper edges and open at their lower ends, and a disk-like reinforcement member 31 is fixed to lower end faces of a lower end part of the protection tube 6, so that an exposed part of a solid electrolyte tube 4 has its lower end upwardly spaced from the reinforcement member 31, permitting an enhanced replacement of molten metal.

In the measuring portion of FIG. 8B, a similar protection tube 6 has a reinforcing annular or strip member 32 fitted or wound thereon, at a position vicinal to lower edges of a lower end part of the protection tube 6. The reinforcing member 32 has a designed height so that a lowermost part of a partially exposed electrolyte tube 4 is thereby masked, permitting a decreased dynamic load to be imposed on the exposed part of tube 4. A plurality of such reinforcing members may preferably be fitted or wound on a lower end part of the protection tube 6.

FIGS. 9A to 9E show exemplary combinations of modified external protection tubes and modified bottom reinforcement members.

Figure 9A:
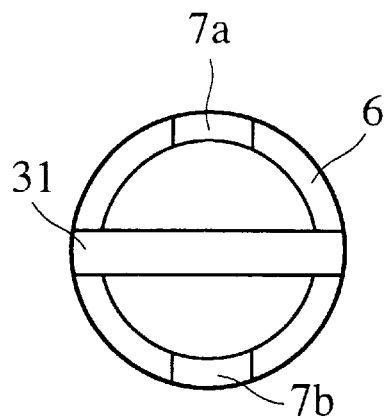
FIGS. 9A to 9E are bottom views of measuring portions of oxygen measuring probes according to modifications of the embodiment of FIG. 6, respectively, as they are applicable to other embodiments and modifications thereof.

In an example shown in FIG. 9A, a protection tube 6 has a downwardly open front slot 7a and an analogous rear slot 7b formed in a lower end part thereof, and an elongate reinforcement plate 31 is fixed at both ends thereof to arcuate lower edges of the lower end part of tube 6, bridging symmetrically selected points thereon, permitting an increased rigidity to have an increased slot width.

Figure 9B:
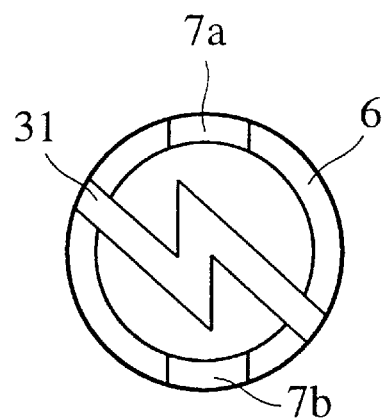

In an example shown in FIG. 9B, a similar protection tube 6 is reinforced at its lower end with a zigzag-shaped reinforcement member 31 bridging symmetrical points on lower edges of the tube 6, permitting an increased rigidity and a controlled flexibility for a laterally expanding deformation.

Figure 9C:
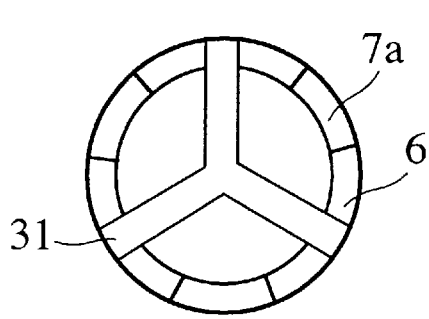

In an example shown in FIG. 9C, a protection tube 6 has a tripe of symmetrically arranged downwardly open slots 7a formed in a lower end part thereof, and a star or Y-shaped reinforcement plate 31 is fixed at ends of its three stems to arcuate lower edges of the lower end part of tube 6, bridging symmetrical points thereon, permitting an increased rigidity. Each slot 7a or each stem may be opposed to a running direction of molten metal.

Figure 9D:
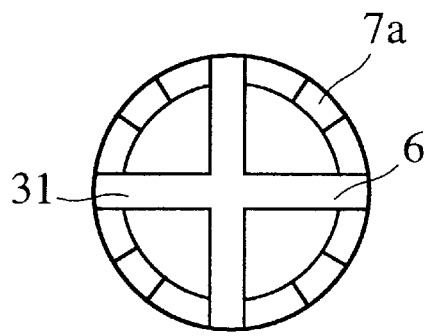

In an example shown in FIG. 9D, a protection tube 6 has a total of four symmetrically arranged downwardly open slots 7a formed in a lower end part thereof and a cross-like reinforcement plate 31 is fixed at ends of its four stems to arcuate lower edges of the lower end part of tube 6, bridging symmetrical points thereon, permitting an increased rigidity. In this example also, each slot 7a or each stem may be opposed to a running direction of molten metal.

Figure 9E:
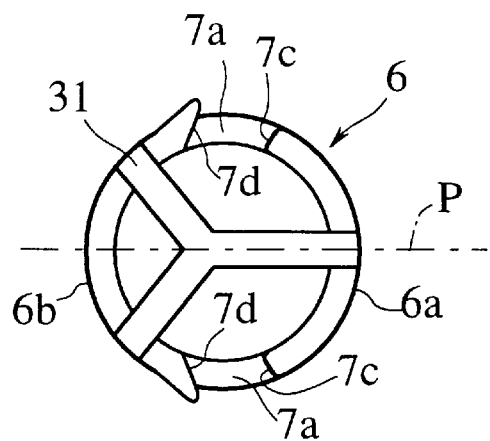

In an example shown in FIG. 9E, a protection tube 6 has a pair of downwardly open lateral slots 7a symmetrical to each other with respect to an imaginary plane P parallel to a running direction of molten metal, and a Y-shaped reinforcement plate 31 is fixed at an end of its front stem to an arcuate edge of a front wall 6a and at ends of its rear stems to an arcuate edge of a rear wall 6b, bridging symmetrical points thereon, permitting a directionally increased rigidity. Each slot 7a has a front side 7c thereof frontwardly tapered and chamfered along its inner and outer edges, and a rear side 7d thereof frontwardly tapered, outwardly bulged or projected over length of its outer edge, and chamfered over length of its inner edge. Molten metal is deflected by the outer edge of the rear side 7d of each slot 7a, and inflows through each slot 7a inside the protection tube 6, and downwardly advances to go out through openings defined between the reinforcement member 31 and the lower edges of the tube 6.

Figure 10A:
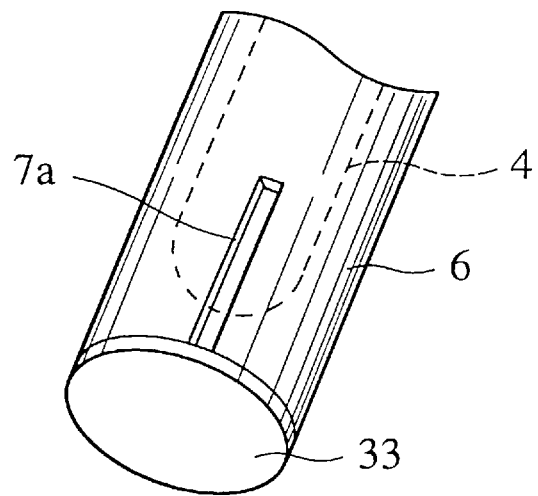
FIGS. 10A and 10B are partial perspective views of measuring portions of oxygen measuring probes according to modifications of the embodiment of FIG. 6.
Figure 10B:
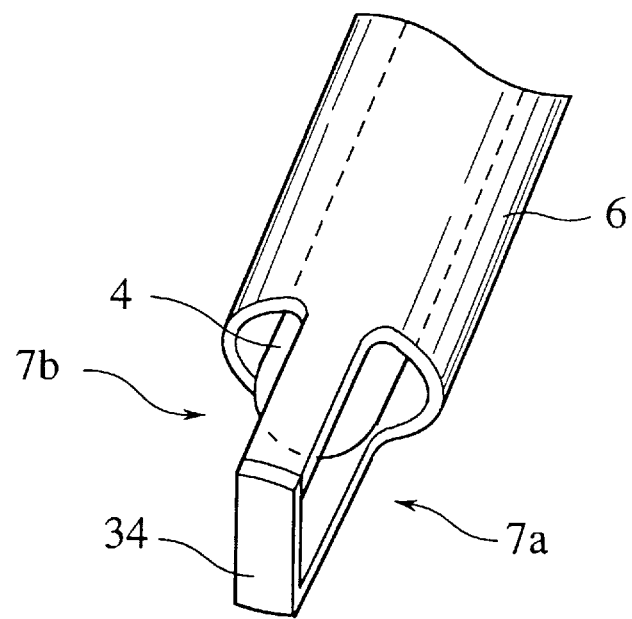

FIGS. 10A and 10B also show exemplary combinations of external protection tubes and bottom reinforcement members.

In an example shown in FIG. 10A, a protection tube 6 has a pair of downwardly open 2 mm-width slots 7a formed in a lower end part thereof, and is closed to be reinforced by a relatively thin disc plate 33 fixed to edges of the lower end part of tube 6.

In an example shown in FIG. 10B, a protection tube 6 has a pair of downwardly open slots 7a formed in a lower end part thereof with a 70% circumferential width in total, and is reinforced by a relatively thick elongate chip plate 34 fixed at its both ends to widths of edges of the lower end part of tube 6.

Such reinforcement members may be fitted in a lower end part of an external protection tube.

Figure 11:
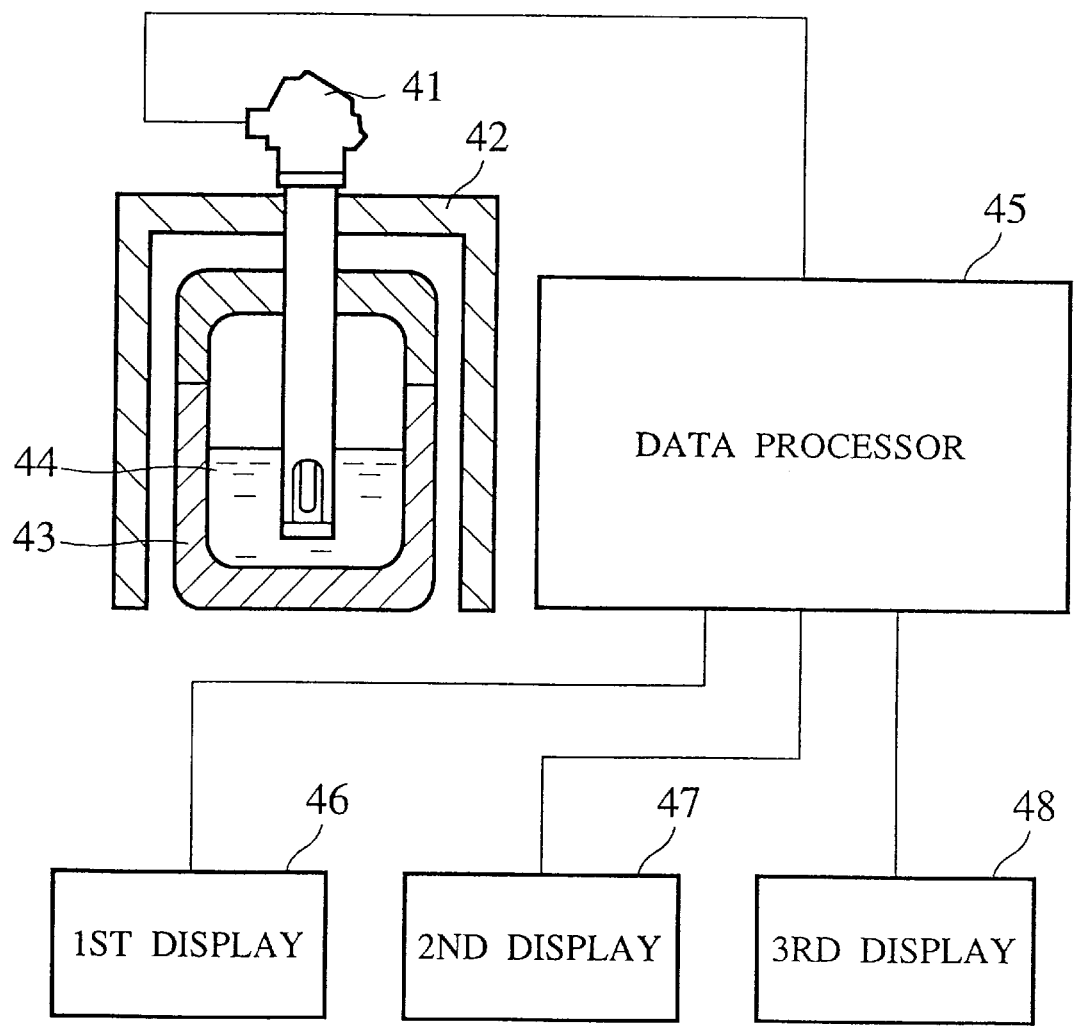
FIG. 11 is a schematic block diagram of a probe device according to another embodiment of the invention.

FIG. 11 is a schematic block diagram of an entire system of a probe device according to a second embodiment of the invention.

In this embodiment, a body 44 of molten copper runs in a totally enclosed rectangular runner 43 connected to a copper wire continuous casting and rolling section, and a probe support frame 42 is built in place, standing astride. A head member of the supprt frame 42 holds an oxygen measuring probe 41 analogous to the probe 1 of the first embodiment, which probe 41 has a measuring portion thereof inserted through a cover member of the runner 43 and dipped in the running molten copper 44, to such a depth that a surface of the molten copper extends at a level vicinal to an upper end of a front slot formed in a lower end part of an external protection tube of the probe 41.

The probe 41 works to measure a potential difference representative of an emf across a wall of an electrolyte tube and another potential difference as the temperature signal representative of a temperature of streams of molten copper 44 in contact with the electrolyte tube, which potential differences are sampled as data to be input to a data processor 45, where they are processed for arithmetic operations to determine a current activity $a_0$ of oxygen in molten copper 44 and a current temperature of the molten copper 44 in a real-time manner.

Letting E be a sampled emf, and T be an absolute temperature corresponding to the temperature signal, the oxygen activity $a_0$ of molten copper 44 is calculated such that:

$$a_0 = exp[-\Delta G^0/RT] \cdot \{(P_0^{1/4} + P_{ref}^{1/4})exp[-EF/RT] - P_8^{1/4}\}^2,$$

where R is a gas constant, F is a Faraday constant, $P_8$ is a partial pressure of oxygen for an ionic conduction to be equivalent to an electronic conduction, $P_{ref}$ is an equilibrium partial pressure of oxygen to an employed reference material, and $\Delta G^0$ is a variation of Gibbs' free energy associated with a dissolution of oxygen to molten copper.

Figure 12:
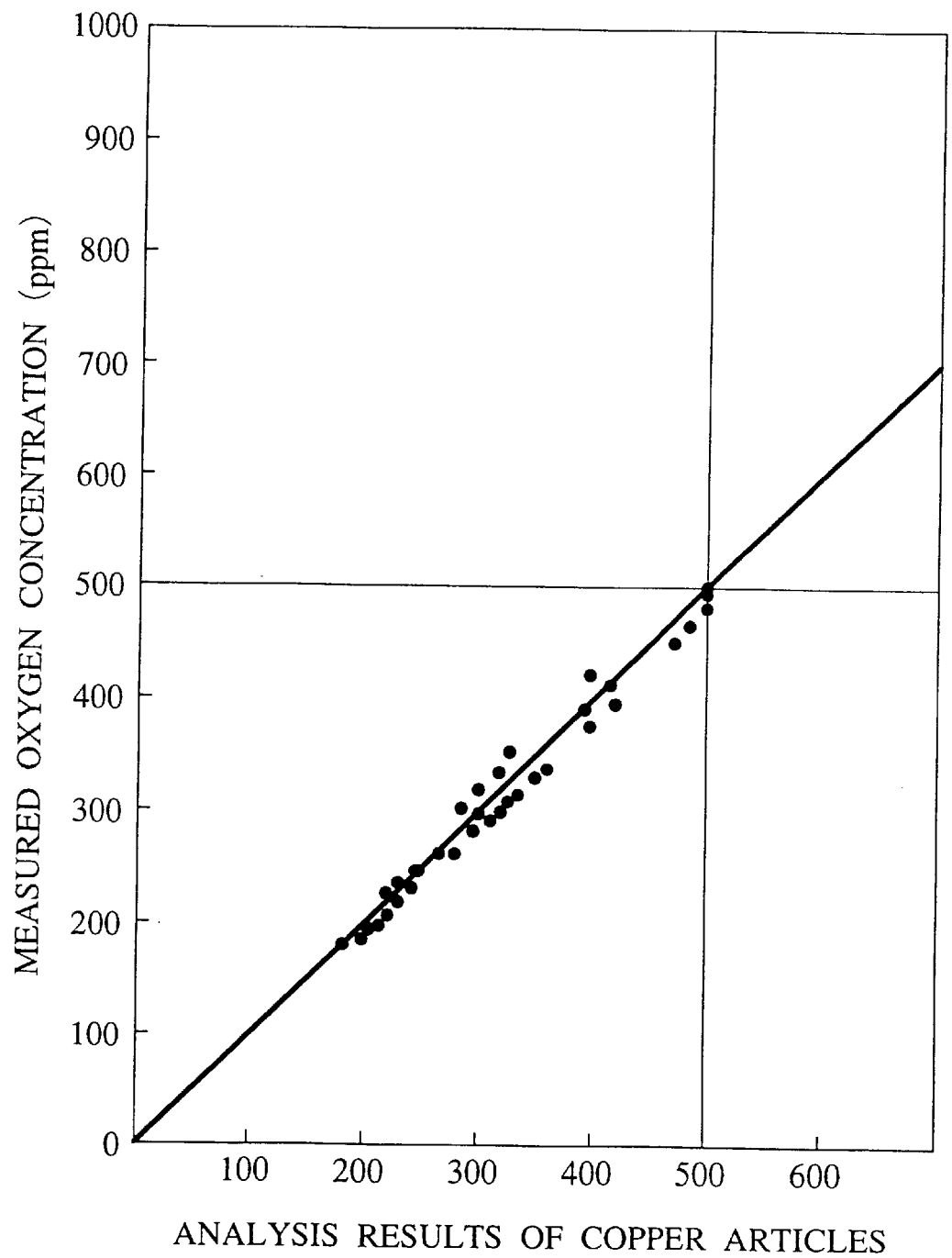
FIG. 12 is a graph comparing a set of measured data on oxygen concentrations of molten metal with a set of analysis data on oxygen concentrations of articles casted from the molten metal.

Such physicochemical values are known or reported by authorities. The oxygen activity $a_0$ represents an oxygen concentration in terms of a mol ratio in molten copper, which may be compensated in accordance with a composition of the molten metal and/or kinds of raw materials, as necessary. As the equilibrium oxygen partial pressure $P_{ref}$, a Kubaschewski's value may preferably be employed to ensure a matching oxygen concentration between a probe measurement to a running body of molten copper and a gas chromatgraphic analysis of copper wires made from the molten copper, as illustrated in FIG. 12 in which an ordinate represents a measured oxygen concentration and an abscissa represents an analysis result.

The data processor 45 outputs processed results to a first display 46 which displays an oxygen activity, a second display 47 which displays the oxygen activity and a molten copper temperature, and/or a third display 48 which displays an oxygen concentration and the molten copper temperature. The oxygen measurement and/or data sampling may be continuous or intermittent, as circumstances require.

The probe 41 may be installed at a number of measuring points along the runner 43, and a combination of displays 46/47/48 may be provided at a number of places along a wire continuous casting and rolling line to permit a real-time check and a stable operation, allowing conforming articles to be produced with a quality and at a high precision due to exact information on oxygen concentration and molten copper temperature.

For a preferable measurement possibly covering depth and width of a running body 44 of molten copper, the probe 41 may be located in place where the runner 43 is narrowed e.g. to a 150-mm width, and dipped in the running molten copper to a sufficient depth, e.g. to a 100-mm depth.

A solid electrolyte tube with an exemplary 100-mm length may preferably have a dipped length greater than 10 mm to detect a significant oxygen activity. For a better average, the dipped length may preferably be limited between 25 mm to 80 mm, ensuring that a body of fixative material is kept free from occasional contact with molten copper.

There will be described two related experiments and their results, with reference to FIGS. 13 and 14.

Experiment-1

Figure 13:
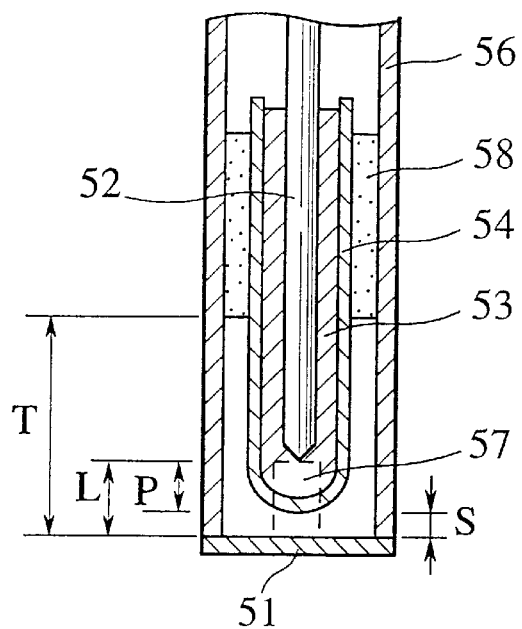
FIG. 13 is a longitudinal section of a measuring portion of an oxygen measuring probe according to another embodiment of the invention without an internal protection tube.

An experiment-1 was performed by using a total of nine oxygen measuring probes that had no internal protection tubes, as shown in FIG. 13. In the nine probes, their measuring portions had a central solid electrolyte tube 54 made of zirconia and closed at a lower end, and a sheathed thermocouple 52 inserted therein at a lower end part thereof, with a body 53 of reference material filled therebetween. The reference material contained Mo and $MoO_2$, which material may be otherwise composed. The electrolyte tube 54 was fixed in an external protection tube 56, with a body 58 of fixative material filled therebetween. The fixative material was a refractory cement, which may be substituted by an arbitrary adequate material. The protection tube 56 had a total of two, three, four or six donwardly open slots 57 formed in a lower end part thereof, with a height L. Among the nine probes, a total of six had a disk-like reinforcement member 51 fixed to lower edges of the lower end part of tube 56.

The electrolyte tube 54 had an ID (inside diameter) of 6 mm and an OD of 10 mm, defining a wall 2-mm thick. The protection tube 56 was 21 mm in ID and 25 mm in OD, of which a 70% circumferential length was 54.98 mm. The fixative material 58 was set at a high position so that the lower edges of the protection tube 56 were downwardly off at a distance T of 30 mm from an underside of the fixative material 58. The electrolyte tube 54 was long enough to have a bottom part thereof exposed via the slots 57, so that a lowermost end of the tube 54 was at a vertical distance S of 5 mm from the lower edges of the tube 56. The bottom part of tube 54 had an exposed length P of 5 mm in one probe or 10 mm in the remaining eight probes.

The slots 57 had a width of 2 mm, 2.5 mm, 5 mm, 8 mm, 9 mm, or 10 mm, as listed in Table-1 on the next page.

The nine probes were numbered to be identified, and tested for a continuous measurement one after another, by dipping in molten copper running at a speed of approx. 1 m/min.

The molten copper ran along the runner 43, entering a wire production line, where it was casted and rolled to be roughly drawn into an endless copper wire of a 8-mm diameter, which was cut at intervals of a predetermined length to be wound into a sequence of wire coils with a 2.5-mm width and a 5-mm thick, which coils were each taken for a sampling to provide a vacuum sample (V.S.).

V.S. analysis data were handled in a statistic manner to provide reference values by probes, and each probe was evaluated in terms of a degree of dispersion (σ%) of displayed values relative to an associated reference value and categorized (see Table-1) to be:

"V (very good)" for a range of $|σ\%| \leq 3.0$;

"G (good)" for a range of $3.0 < |σ\%| \leq 4$;

"C (conforming)" for a range of $4 < |σ\%| \leq 5$; or

"N (non-conforming)" for a range of $|σ\%| > 5$.

Moreover, respective probes were evaluated in respect of a withstanding time (tw) for a practical measurement and categorized (see Table-1) to be:

"G (good)" for a range of $tw \geq 30$ hrs;

"C (conforming)" for a range of $30 \text{ hrs} > tw \geq 10$ hrs; or

"N (non-conforming)" for a range of $tw < 10$ hrs.

TABLE 1

| Probe id: | 1 | 2 | 3 | 4 | 5 | 6 | 7 | 8 | 9 |
|---|---|---|---|---|---|---|---|---|---|
| Reinforced: | no | no | no | yes | yes | yes | yes | yes | yes |
| Slots, | | | | | | | | | |
| Number: | 4 | 2 | 2 | 4 | 3 | 2 | 4 | 6 | 6 |
| Width, mm: | 2 | 10 | 10 | 2.5 | 5 | 10 | 10 | 8 | 9 |
| Total, mm: | 8 | 20 | 20 | 10 | 15 | 20 | 40 | 48 | 54 |
| %-width to circum. | 10.2 | 25.5 | 25.5 | 12.7 | 19.1 | 25.5 | 51 | 61.1 | 68.8 |
| P, mm: | 10 | 5 | 10 | 10 | 10 | 10 | 10 | 10 | 10 |
| Categories, | | | | | | | | | |
| σ %: | C | N | G | C | G | G | G | G | G |
| tw: | N | C | N | G | G | G | G | C | C |

As will be seen from the Table-1, a fifth to a seventh probe were good in both σ% and tw, a fourth to a ninth, good or conforming in both σ% and tw, and all of a first to the ninth, good or conforming in either σ% or tw. The first to a third were not reinforced. However, a conformity in tw was observed of a second that had a smaller exposed length P, which measured a shallow region of molten copper with an increased tendency to have a varying high oxygen concentration, an elongated time to achieve an equilibrium and a significant frequency of floatings such as slag. The first and the fourth were small in slot width, with a reduced accuracy. An eighth and the ninth had a greater number of slots than others, with a reduced durability.

Experiment-2

Figure 14:
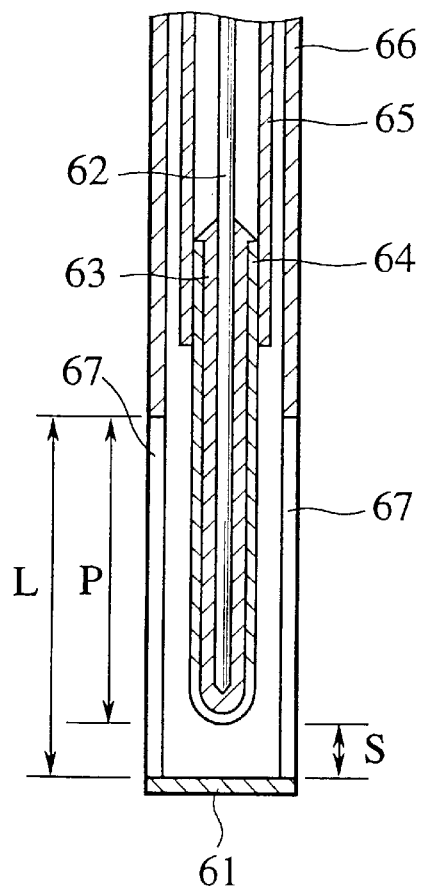
FIG. 14 is a longitudinal section of a measuring portion of an oxygen measuring probe with an internal protection tube according to a modification of the embodiment of FIG. 6.

An experiment-2 was performed by using a total of 15 oxygen measuring probes that had an internal protection tube 65, as shown in FIG. 14. In the 15 probes, their measuring portions had a central solid electrolyte tube 64 closed at a lower end, and a sheathed thermocouple 62 inserted therein at a lower end part thereof, with a body 63 of reference material filled therebetween. The reference material contained Mo and MoO$_2$, which material may be otherwise composed. An upwardly extending remaining part of the theathed thermocouple 62 was enclosed by the internal protection tube 65. The electrolyte tube 64 was fixed at an upper end part thereof to a lower end part of the internal protection tube 65, with an unshown body of fixative material filled therebetween. The internal protection tube 65 and the electrolyte tube 64 were enclosed by an external protection tube 66 and indirectly fixed thereto like the first embodiment. The external protection tube 66 had a total of two, three, four or six donwardly open slots 67 formed in a lower end part thereof, with a height L. Among the 15 probes, a total of 12 had a disk-like reinforcement member 61 fixed to lower edges of the lower end part of tube 66.

The electrolyte tube 64 had an ID of 6 mm and an OD of 8 mm, defining a wall 1-mm thick. The external protection tube 66 was 16 mm in ID and 21.7 mm in OD, of which a 70% circumferential length was 47.72 mm. The electrolyte tube 64 was long enough to have a bottom part thereof exposed via the slots 67, so that a lowermost end of the tube 64 was at a vertical distance S of 8 mm from the lower edges of the tube 66. The bottom part of tube 64 had an exposed length P of 5 mm in one probe, 10 mm in four probes, 12 mm in one probe, 30 mm in three probes, 40 mm in four probes, 50 mm in one probe, or 60 mm in one probe, and the slots 67 had a width of 1 mm, 3 mm, 9 mm, 10 mm, 11 mm, or 13 mm, as listed in Table-2.

The 15 probes were numbered to be identified, starting from a 10th, and tested for a continuous measurement one after another, by dipping in molten copper running at a speed of approx. 1 m/min, with results shown in Table-2.

The runner, dipping method, measurement procedure, copper production line, sampling, V.S. analysis data handling, probe evaluation and definition of categories were identical to those of the experiment-1.

TABLE 2

| Probe id: | 10 | 11 | 12 | 13 | 14 | 15 | 16 | 17 | 18 |
|---|---|---|---|---|---|---|---|---|---|
| Reinforced: | no | no | no | yes | yes | yes | yes | yes | yes |
| Slots, | | | | | | | | | |
| Number: | 4 | 2 | 2 | 6 | 4 | 4 | 2 | 2 | 2 |
| Width, mm: | 3 | 10 | 10 | 1 | 13 | 3 | 10 | 10 | 10 |
| Total, mm: | 12 | 20 | 20 | 6 | 52 | 12 | 20 | 20 | 20 |
| %-width to circum. | 17.6 | 29.4 | 29.4 | 7.1 | 72.5 | 17.6 | 29.4 | 29.4 | 29.4 |
| P, mm: | 12 | 5 | 10 | 40 | 30 | 40 | 10 | 50 | 60 |
| Categories, | | | | | | | | | |
| σ %: | C | N | C | N | G | G | G | V | V |
| tw: | N | C | N | G | N | G | G | G | G |

TABLE 2-continued

| Probe id: | 19 | 20 | 21 | 22 | 23 | 24 |
|---|---|---|---|---|---|---|
| Reinforced: | yes | yes | yes | yes | yes | yes |
| Slots, | | | | | | |
| Number: | 2 | 4 | 4 | 4 | 4 | 3 |
| Width, mm: | 13 | 9 | 9 | 11 | 11 | 10 |
| Total, mm: | 26 | 36 | 36 | 44 | 44 | 30 |
| %-width: | 38.1 | 52.8 | 52.8 | 64.5 | 64.5 | 44.1 |
| to circum. | | | | | | |
| P, mm: | 40 | 10 | 30 | 10 | 30 | 40 |
| Categories, | | | | | | |
| σ %: | V | G | V | G | V | V |
| tw: | G | G | C | G | C | G |

As will be seen from the Table-2, a 15th to a 20th, a 22nd and a 24th probe were very good or good in both σ% and tw, a 21st and a 23rd, good or conforming in both σ% and tw, and all of the 10th to the 24th, very good or good or conforming in either σ% or tw. The 10th to a 12th were not reinforced. However, a conformity in tw was observed of an 11th that had a smaller exposed length P, like the second probe in the experiment-1. A 14th, the 21th and the 23th had large %-widths to an outer circumference of the external protection tube 66, with reduced rigidities, respectively. A 13th had a small slot width with a reduced measurement accuracy.

As a result, advantages of the 31st aspect were confirmed.

Figure 15:
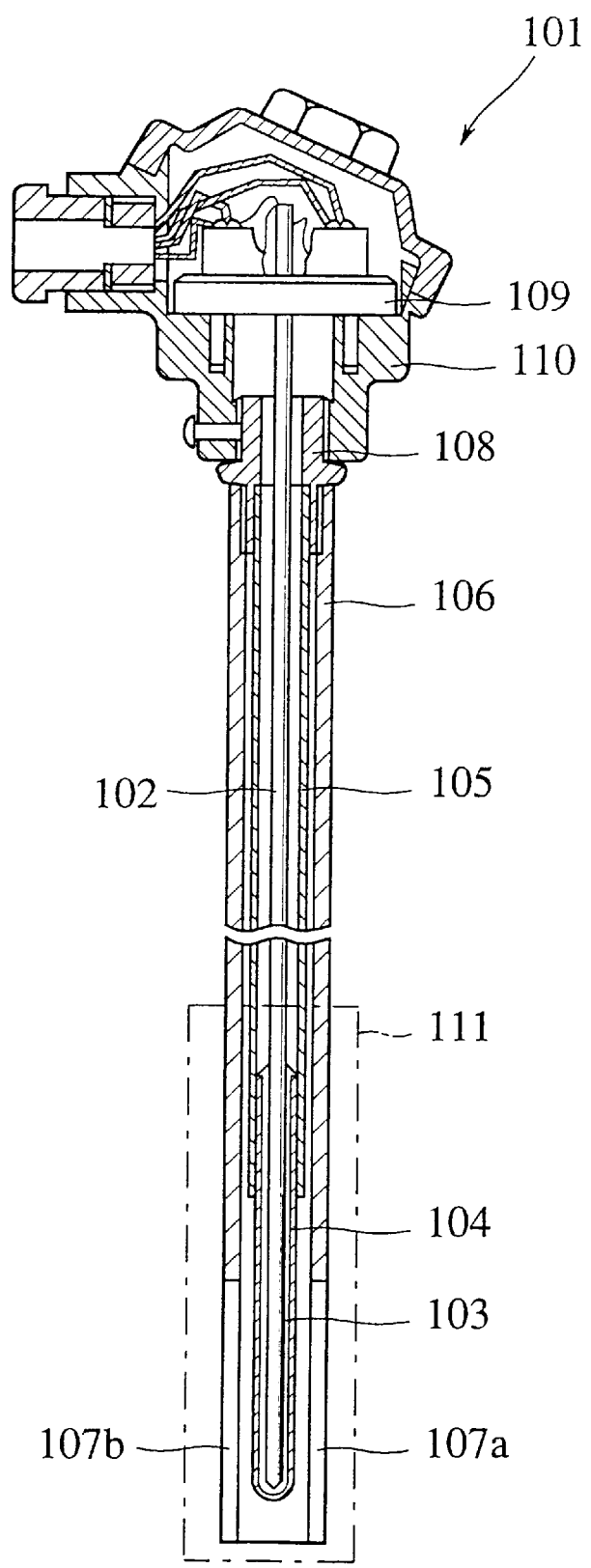
FIG. 15 is a longitudinal section of an oxygen measuring probe of a probe device according to another embodiment of the invention.
Figure 16:
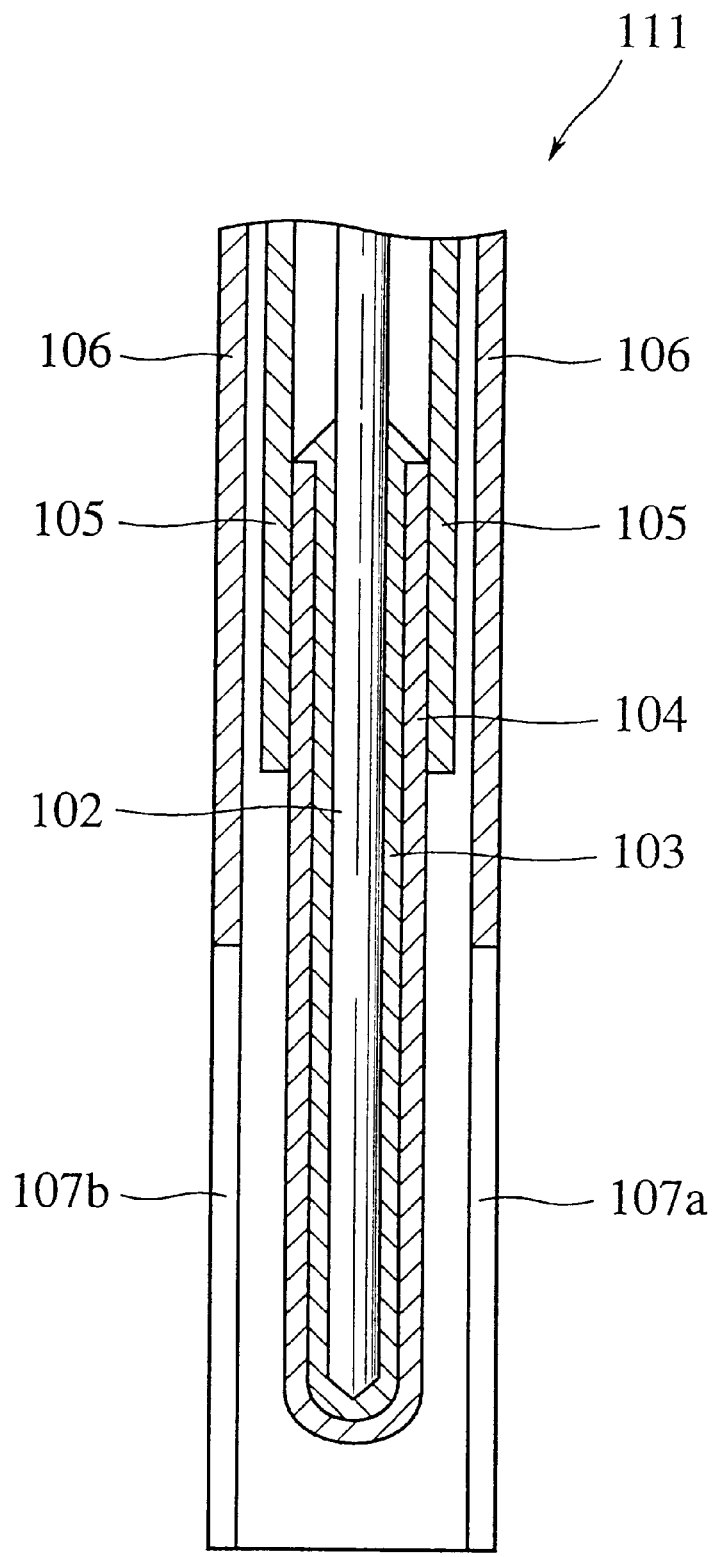
FIG. 16 is an enlarged partial section of a measuring portion of the probe of FIG. 15.

FIG. 15 is a section of an oxygen measuring probe according to a third embodiment of the invention, and FIG. 16, an enlarged partial section of a measuring portion of the probe of FIG. 15.

In FIG. 15, designated at reference character 101 is the probe in concern, and 111 is the measuring portion. The probe 101 is different from the probe 1 of the first embodiment in that it has no reinforcement member (31), as slots 107a, 107b are formed with adequate widths. As shown in FIGS. 15 and 16, the measuring portion 111 includes a central solid electrolyte tube 104 close at its round lower end, and a sheathed thermocouple 102 fitted therein, with a body 103 of reference material filled therebetween.

The sheathed thermocouple 102 is enclosed by an internal protection tube 105, of which a lower end part is fitted to be fixed in an upper end part of the electrolyte tube 104. An upper end part of the internal protection tube 105 is fitted to be fixed in a boss part of a socket 108, of which a head part is screwed to a lower case of a terminal casing 110 that has accommodated therein a terminal block 109. The internal protection tube 105 and the electrolyte tube 104 are enclosed by an external protection tube 106, which is screwed at an upper end part thereof to the boss part of socket 108 and has at a lower end part thereof the slots 107a, 107b formed therein with a downwardly open configuration. The slots 107a, 107b have their widths determined in accordance with the 34th and 35th aspects, and the electrolyte tube 104 has an exposed length determined in accordance with the 36th aspect.

Like the second embodiment, two related experiments were performed for confirmation.

Experiment-3

An experiment-3 similar to the experiment-1 was performed by using a total of 11 oxygen measuring probes of a structure shown in FIG. 13 that had not an internal protection tube (105).

An electrolyte tube 54 had an ID of 6 mm and an OD of 10 mm, of which a ¼ is 2.5 mm and a 5/1 is 2.0 mm. An external protection tube 56 was 21 mm in ID and 25 mm in OD, of which a ⅓ is 8.33 mm and a ⅗ is 15.00 mm. A body 58 of fixative material was set such that lower edges of the protection tube 56 were downwardly off at a distance T of 30 mm from an underside of the fixative material 58. The electrolyte tube 54 had a bottom part thereof exposed via slots 57, so that a lowermost end of the tube 54 was at a vertical distance S of 5 mm from the lower edges of the tube 56. The bottom part of tube 54 had an exposed length P of 5 mm. A dipped length to molten copper was within a range of 11 mm to 20 mm.

The slots 57 had a height L of 10 mm, and a width of 1 mm, 2 mm, 3 mm, 5 mm, 6 mm, 8 mm, 10 mm, 11 mm, 14 mm or 16 mm, as listed in Table-3 below.

TABLE 3

| Probe id: | 101 | 102 | 103 | 104 | 105 |
|---|---|---|---|---|---|
| Reinforced: | no | no | no | no | no |
| Slots, | | | | | |
| Number: | 4 | 2 | 2 | 2 | 2 |
| Width, mm: | 2 | 10 | 3 | 5 | 8 |
| L, mm: | 10 | 10 | 10 | 10 | 10 |
| P, mm: | 5 | 5 | 5 | 5 | 5 |
| Categories, | | | | | |
| σ %: | N | G | C | G | G |
| tw: | G | N | G | G | C |

| Probe id: | 106 | 107 | 108 | 109 | 110 | 111 |
|---|---|---|---|---|---|---|
| Reinforced: | yes | yes | yes | yes | yes | yes |
| Slots, | | | | | | |
| Number: | 4 | 2 | 4 | 4 | 2 | 2 |
| Width, mm: | 1 | 16 | 3 | 6 | 11 | 14 |
| L, mm: | 10 | 10 | 10 | 10 | 10 | 10 |
| P, mm: | 5 | 5 | 5 | 5 | 5 | 5 |
| Categories, | | | | | | |
| σ %: | N | G | G | G | G | G |
| tw: | G | N | G | G | G | C |

As will be seen from the Table-3, a 104th and a 108th to a 110th probe were good in both σ% and tw, a 103rd and 105th and a 111th, good or conforming in both σ% and tw, and all of a 101st to the 111th, good or conforming in either σ% or tw. The 101st to the 105th were not reinforced. The 103rd to the 105th and the 108th to the 111th had widths according to the concerned aspects, while that of the 103rd was relatively narrow and those of the 105th and the 111th were relatively wide, so that these probes had a reduced measurement accuracy or a reduced durability.

Experiment-4

An experiment-4 similar to the experiment-2 was performed by using a total of 13 oxygen measuring probes of a structure shown in FIG. 14 that had an internal protection tube 65.

An electrolyte tube 64 had an ID of 6 mm and an OD of 8 mm, of which a ¼ is 2.0 mm and a ⅕ is 1.6 mm. An external protection tube 66 was 16 mm in ID and 21.7 mm in OD, of which a ⅓ is 7.23 mm and a ⅗ is 13.02 mm. The electrolyte tube 64 was long enough to have a bottom part thereof exposed via slots 67, so that a lowermost end of the tube 64 was at a vertical distance S of 8 mm from lower edges of the tube 66. The bottom part of tube 64 had an exposed length P of 42 mm. A dipped length to molten copper was within a range of 51 mm to 80 mm.

The slots 67 had a height L of 50 mm, and a width of 1 mm, 3 mm, 4 mm, 5 mm, 8 mm, 10 mm, 13 mm or 15 mm, as listed in Table-4 on the next page.

As will be seen from the Table-4, a 115th and a 116th and a 119th to a 124th probe were very good or good in both σ% and tw, a 114th, good or conforming in both σ% and tw, and all of a 112th and the 114th to the 124th, good or conforming in either σ% or tw.

The 112th to a 116th, including the 114th, were not reinforced. Moreover, the 112th had a relatively small slot width, and a 113th had a relatively large slot width. The 112th and the 114th had their slots 67 deformed in a close direction. The 113th had its lower end part deformed, disturbing streams of molten copper, resulting in a breakage of the electrolyte tube 64. A 117th had a relatively small slot width with a reduced measurement accuracy. A 118th had a relatively large slot width with a reduced rigidity.

As a result, advantages of the 34th to the 36th aspect were confirmed.

TABLE 4(1/2)

| Probe id:   | 112 | 113 | 114 | 115 | 116 |
|-------------|-----|-----|-----|-----|-----|
| Reinforced: | no  | no  | no  | no  | no  |
| Slots,      |     |     |     |     |     |
| Number:     | 4   | 2   | 4   | 2   | 2   |
| Width, mm:  | 1   | 8   | 3   | 5   | 4   |
| L, mm:      | 50  | 50  | 50  | 50  | 50  |
| P, mm:      | 42  | 42  | 42  | 42  | 42  |
| Categories, |     |     |     |     |     |
| σ %:        | N   | N   | C   | G   | G   |
| tw:         | C   | N   | G   | G   | G   |

TABLE 3(2/2)

| Probe id:   | 117 | 118 | 119 | 120 | 121 | 122 | 123 | 124 |
|-------------|-----|-----|-----|-----|-----|-----|-----|-----|
| Reinforced: | yes | yes | yes | yes | yes | yes | yes | yes |
| Slots,      |     |     |     |     |     |     |     |     |
| Number:     | 4   | 2   | 4   | 2   | 2   | 3   | 2   | 2   |
| Width, mm:  | 1   | 15  | 3   | 5   | 8   | 8   | 10  | 13  |
| L, mm:      | 50  | 50  | 50  | 50  | 50  | 50  | 50  | 50  |
| P, mm:      | 42  | 42  | 42  | 42  | 42  | 42  | 42  | 42  |
| Categories, |     |     |     |     |     |     |     |     |
| σ %:        | N   | V   | G   | V   | V   | V   | V   | V   |
| tw:         | G   | N   | G   | G   | G   | G   | G   | G   |

FIGS. 17A to 17F show exemplary combinations of modified front slots and a representative reinforcement. It will be seen that a corresponding rear slot may be provided.

Figure 17A:
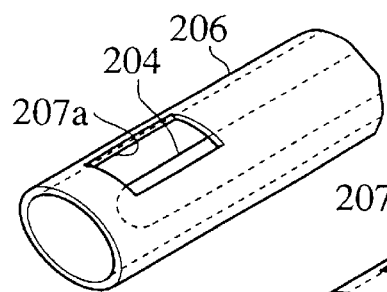
FIGS. 17A to 17F are partial perspective views of measuring portions of oxygen measuring probes according to modifications of the embodiments of FIGS. 6 and 15, as they are applicable to other embodiments and modifications thereof.

In an example shown in FIG. 17A, a protection tube 206 has a rectangular front slot 207a, where an electrolyte tube 204 is exposed. No reinforcement member is provided.

Figure 17B:
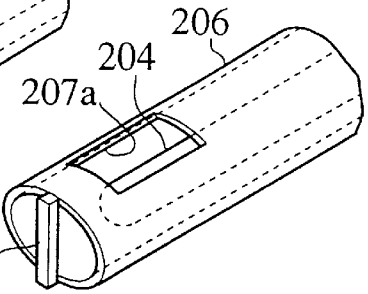

In an example shown in FIG. 17B, a similar protection tube 206 is reinforced by a member 231 extending in parallel to running molten metal.

Figure 17C:
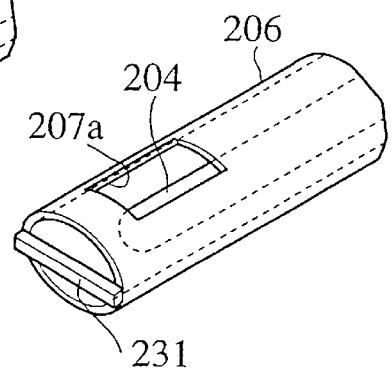

In an example shown in FIG. 17C, a similar protection tube 206 is reinforced by a member 231 extending in a crossing direction to running molten metal.

Figure 17D:
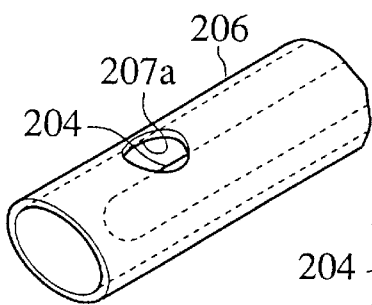

In an example shown in FIG. 17D, a protection tube 206 has a circular front slot 207a, where an electrolyte tube 204 is exposed. No reinforcement member is provided.

Figure 17E:
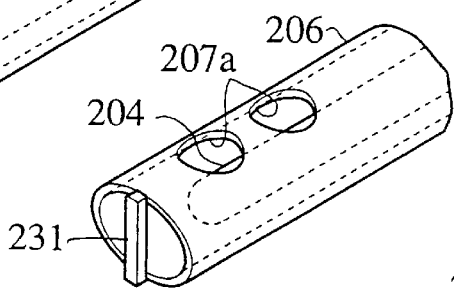

In an example shown in FIG. 17E, a protection tube 206 is formed with a pair of vertically aligned circular slots 207a and reinforced by a member 231 extending in parallel to running molten metal.

Figure 17F:
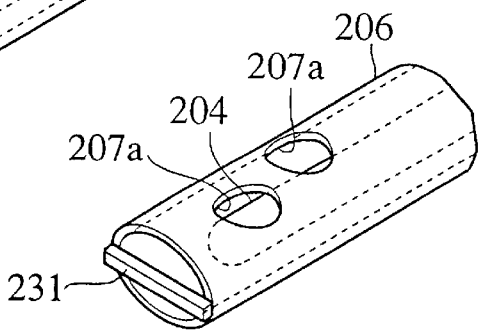

In an example shown in FIG. 17F, a protection tube 206 is formed with a pair of obliquely aligned circular slots 207a and reinforced by a member 231 extending in a crossing direction to running molten metal.

Figure 18A:
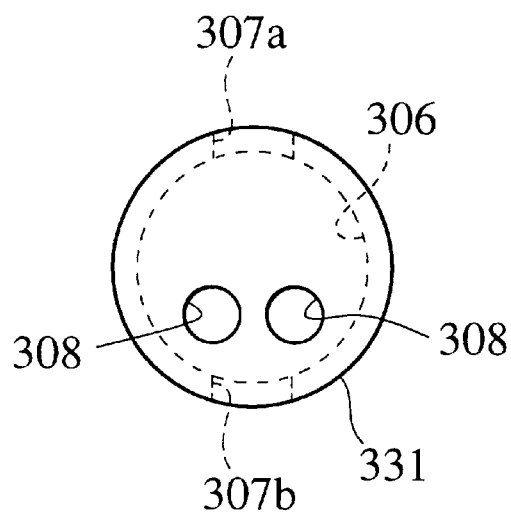
FIGS. 18A and 18B are bottom views of measuring portions of oxygen measuring probes according to variations of the diverse modifications.
Figure 18B:
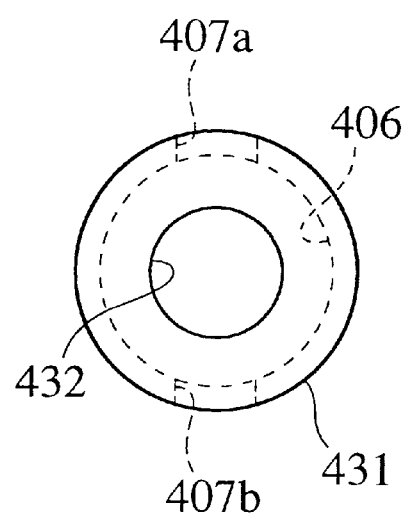

FIGS. 18A and 18B show exemplary combinations of modified reinforcement members and a representative external protection tube.

In an example shown in FIG. 18A, a reinforcement member 331 of a disk form has a pair of circular holes 308 formed in a rear half thereof for letting molten copper go out therethrough, and is fixed to a lower end of an external protection tube 306 which has a pair of front and rear slots 307a, 307b.

In an example shown in FIG. 18B, a reinforcement member 431 of a disk form has a central circular hole 432 formed therein for letting molten copper flow therethrough, and is fixed to a lower end of an external protection tube 406 which has a pair of front and rear slots 407a, 407b.

Figure 19:
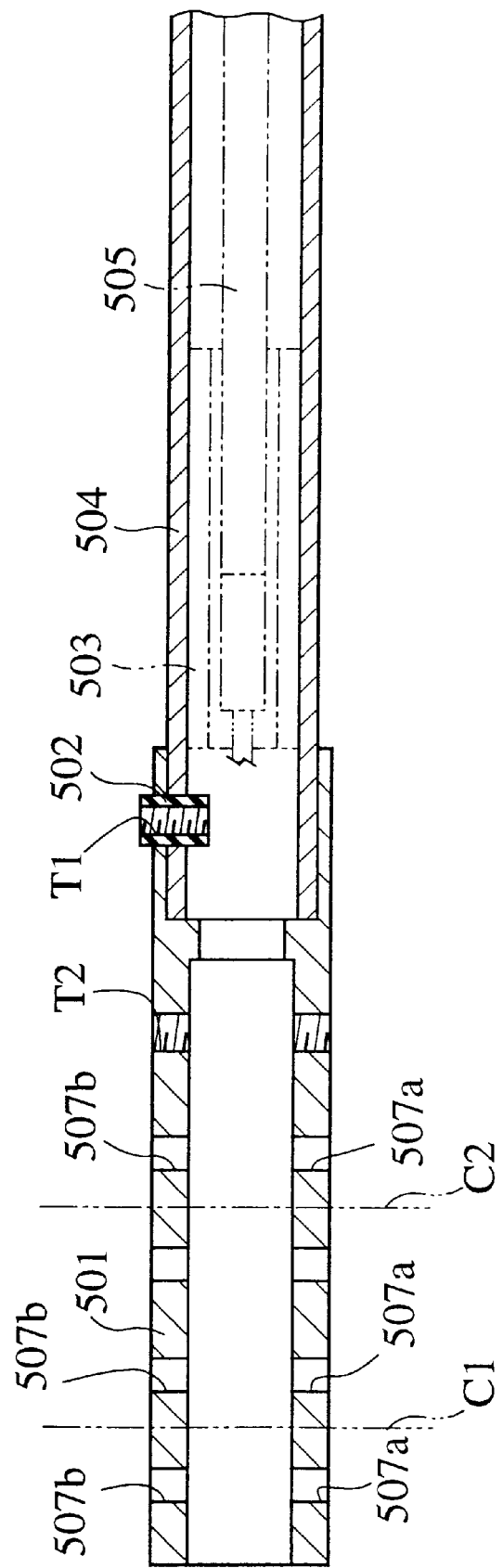
FIG. 19 is a partial longitudinal section of an external protection tube of an oxygen measuring probe of a probe device according to another embodiment of the invention.

FIG. 19 is a partial longitudinal section of an external protection tube of an oxygen measuring probe of a probe device according to a fourth embodiment of the invention.

In this embodiment, the external protection tube comprises an upper tube 504 and a separable lower tube 501. The upper tube 504 has a guide member 503 installed therein, and a slidable internal protection tube 505 fitted therethrough, which tube 505 has an unshown solid electrolyte tube fixed at a distal end thereof. The lower tube 501 is fitted to be detachably attached at an upper end thereof to a lower end of the upper tube 504 by using a boss member 502 laterally inserted therethrough, which member 502 has threads T1 cut therein for applying an unshown screw as a stopper. Like threads T2 may be cut in an upper part of the lower tube 501.

The lower tube 501 is relatively long, and has a plurality of multi-staged pairs of front and rear slots 507a, 507b, so that it may be cut at an adequate position C1 or C2 for a reuse or for a length adjustment.

Figure 20:
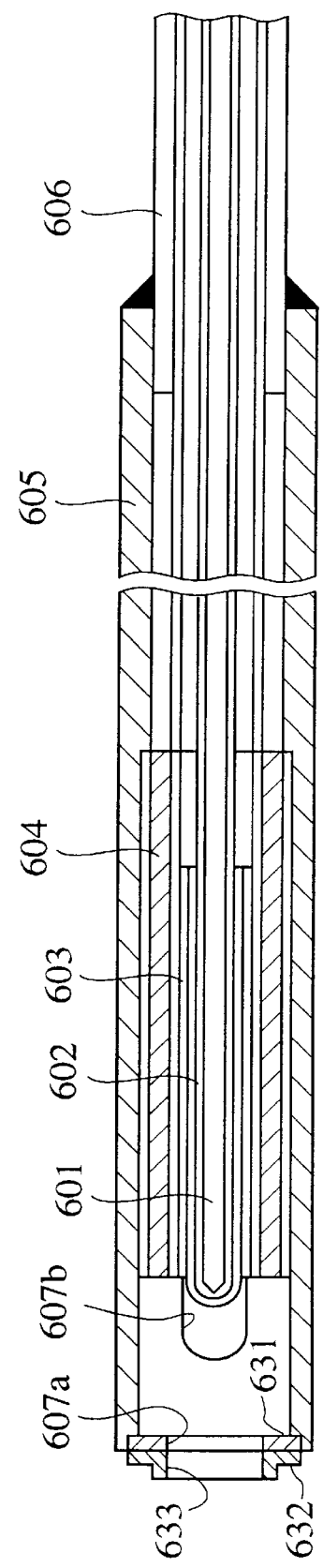
FIG. 20 is a partial longitudinal section of an oxygen measuring probe of a probe device according to another embodiment of the invention.

FIG. 20 is a partial longitudinal section of an oxygen measuring probe of a probe device according to a fifth embodiment of the invention.

In this embodiment, a lower tube member 605 of an external protection tube 606 has at a lower end part thereof a disc plate 631 fitted therein as a reinforcement member. The disc plate 631 has on an underside thereof an arcuate deflector 632 fixed thereto and shaped so as to define a semi-cylindrical surface 633 as a guide groove for guiding part of running molten metal. The disc plate 631 is formed with a central opening 607a for letting streams of the guided part of molten metal inflow there through. The inflowing streams of molten metal are retained as they advance to go out through a rear slot 607b formed in the lower end part of the tube member 605.

The lower tube member 605 has installed therein a lower internal protection tube 604, which accommodates therein a solid electrolyte tube 602, with an annular space 603 left therebetween. The electrolyte tube 602 has a lower end part of a sheathed thermocouple 601 inserted therein, with a body of reference material filled therebetween.

Incidentally, in application of the embodiments described, the solid electrolyte tube with a sheathed thermocouple inserted therein is not simply filled with a body of reference material.

More specifically, as shown in FIG. 7, the reference electrode 3 comprises a body 3a of reference material filled up to a height exceeding a desirable dip length of the solid electrolyte tube 4, a body 3b of alumina powder or other oxidation-preventive material stuffed up to a height near an upper edge of the electrolyte tube 4, and a body 3c of sealing material applied thereover that may be part of the fixative material 5a. The stuffed material 3b should have a lower oxygen equilibrium partial pressure than the reference material 3a.

In this connection, some kinds of refractory cement tend to have a suddenly reduced insulation property over 400° C., and becomes semi-conductive over 600° C. However, the alumina powder can serve as an insulating material even in a hot temperature range.

While preferred embodiments of the present invention have been described using specific terms, such description is for illustrative purposes, and it is to be understood that changes and variations may be made without departing from the spirit or scope of the following claims.

What is claimed is:

1. A probe device vertically partially dipped in running molten metal in a runner for a continuous measurement of oxygen in the running molten metal, the probe device comprising:

a vertically extending cylindrical first tube member made of a solid electrolyte material and closed at a lower end thereof;

a reference electrode contacting an inside of the first tube member;

detection means for detecting a potential difference between a first node connected to the reference electrode and a second node;

a vertically extending conductive second tube member connected to the second node, the second tube member coaxially enclosing the first tube member for protection against the running molten metal and having an open bottom region;

a vertically elongated first slot formed in a first region of a lower wall part of the second tube member and communicating with the open bottom region;

a vertically elongated second slot formed in a second region of the lower wall part opposing the first region with the first tube member therebetween; and a reinforcing plate partially closing the open bottom region and facing the runner.

2. A probe device according to claim 1, further comprising:

an internal protection tube fixed to the first tube member; and a fixing material fixing an upper end of the first tube member to the internal protection tube, at a higher level than the first and second slots.

3. A probe device according to claim 1, wherein the reinforcing plate is elongated and is fixed to a bottom edge of the second tube member.

4. A probe device according to claim 1, wherein:

the reference electrode comprises a sheathed thermocouple inserted in the first tube member and a reference material containing a metal and an oxide thereof and filled in the first tube member;

the second tube member serves as an external electrode; and the first and second slots each has a width within a range between ⅕ of an outside diameter of the first tube member and a ⅗ of an outside diameter of the second tube member.

5. A probe device according to claim 1, wherein:

the first tube member has an exposed vertical length in the first and second slots; and the first and second slots each has a ratio of vertical length thereof to the exposed vertical length within a range between 7:1 and 7:6.

6. A probe device according to claim 1, further comprising:

processing means for processing data on the potential difference representative of an electromotive force and a temperature signal to determine an oxygen activity and a temperature of the running molten metal; and one of first display means for displaying temporal values of the oxygen activity and the temperature of the running molten metal and second display means for displaying the oxygen activity.

* * * * *